US010705017B2

United States Patent
Muldoon et al.

(10) Patent No.: US 10,705,017 B2
(45) Date of Patent: Jul. 7, 2020

(54) CHARACTERIZATION OF LIQUIDS IN SEALED CONTAINERS

(71) Applicant: Cecilia Muldoon, Oxford (GB)

(72) Inventors: Cecilia Muldoon, Oxford (GB); Edoardo Ceci Ginistrelli, Oxford (GB)

(73) Assignee: VeriVin Ltd., Long Hanborough (GB)

( * ) Notice: Subject to any disclaimer, the term of this patent is extended or adjusted under 35 U.S.C. 154(b) by 0 days.

(21) Appl. No.: 16/003,913

(22) Filed: Jun. 8, 2018

(65) Prior Publication Data

US 2018/0356341 A1    Dec. 13, 2018

Related U.S. Application Data

(60) Provisional application No. 62/517,527, filed on Jun. 9, 2017.

(51) Int. Cl.
*G01N 21/51* (2006.01)
*G01N 21/552* (2014.01)
(Continued)

(52) U.S. Cl.
CPC .......... *G01N 21/51* (2013.01); *G01N 21/552* (2013.01); *G01N 21/65* (2013.01); *G01N 21/01* (2013.01); *G01N 2021/0137* (2013.01); *G01N 2021/1744* (2013.01); *G01N 2021/4709* (2013.01); *G01N 2021/4742* (2013.01)

(58) Field of Classification Search
CPC .............. G01N 33/6872; G01N 21/65; G01N 2201/06113; G01N 33/146; G01N 21/51; G01N 15/1429; G01N 2015/1488; G01N 21/3577; G01N 21/8851; G01N 21/90; G01N 2021/6417; G01N 21/64; G01N 21/6402; G01N 21/8483; G01N 21/41; G01N 21/4133; G01N 33/14; G01N 33/143; G01N 2021/0137; G01N 2021/1744;
(Continued)

(56) References Cited

U.S. PATENT DOCUMENTS 3,858,851 A * 1/1975 Ogle ................ G01N 21/51
                                                      250/564
7,488,940 B2   2/2009 Ohtake et al.
(Continued)

OTHER PUBLICATIONS

International Search Report and Written Opinion for App. Ser. No. PCT/US2018/036762, dated Sep. 18, 2018, 10 pages.
(Continued)

*Primary Examiner* — Michael P Stafira
(74) *Attorney, Agent, or Firm* — Fish & Richardson P.C.

(57) ABSTRACT

A method of illuminating and extracting scattered and transmitted light from a liquid within a sealed glass bottle, the method comprising initiating transmission of an incident light beam from a light source to the sealed bottle, directing the incident light beam to totally internally refract within a wall of the sealed bottle and thereby cause an evanescent wave within the liquid to generate scattered or absorbed light, receiving the scattered or absorbed light from the liquid contained in the sealed bottle, and processing one or more signals representative of the scattered or absorbed light, the signals indicative of one or more molecules indicative of a characteristic being present in the liquid contained in the sealed bottle.

14 Claims, 11 Drawing Sheets

(51) Int. Cl.
*G01N 21/65* (2006.01)
*G01N 21/01* (2006.01)
*G01N 21/17* (2006.01)
*G01N 21/47* (2006.01)

(58) Field of Classification Search
CPC ... G01N 2021/4709; G01N 2021/4742; G01N 21/01; G01N 33/5008; G01N 33/573
See application file for complete search history.

(56) References Cited

U.S. PATENT DOCUMENTS

| | | |
|---|---|---|
| 9,453,826 B2 | 9/2016 | Muldoon |
| 2005/0057798 A1 | 3/2005 | Osborne et al. |
| 2006/0072878 A1 | 4/2006 | Dames et al. |
| 2008/0259313 A1* | 10/2008 | Berndt .................. G01N 21/51 356/39 |
| 2011/0184681 A1 | 7/2011 | Augustine et al. |
| 2017/0032285 A1 | 2/2017 | Sharma et al. |

OTHER PUBLICATIONS

Pipino et al., "Evanescent wave cavity ring-down spectroscopy with total internal reflection minicavity," Rev. Sci. Instrum., 68 (8), Aug. 1997, pp. 2978-2989 [Retrieved Aug. 20, 2018]. Retrieved from internet:<https://ws680.nist.gov/publication/get_pdf.cfm?pub_id=100459>.

* cited by examiner

CHARACTERIZATION OF LIQUIDS IN SEALED CONTAINERS

CLAIM OF PRIORITY

This application claims the benefit of priority under 35 USC § 119(e) to U.S. Provisional Patent Application Ser. No. 62/517,527, filed on Jun. 9, 2017, the entire contents of which are hereby incorporated by reference.

TECHNICAL FIELD

The description relates generally to a non-invasive system for detecting the molecular composition of liquids in sealed containers.

BACKGROUND

The last 20 years have seen growing interest and investment in wine worldwide. With this has come a growing expectation of quality. Unfortunately, like other products, wine can fall victim to external influences that render it defective, e.g., poor production practices, inappropriate storage conditions, etc. Wine is also very complex and tastes differ greatly between individuals, making predicting an enjoyable drinking experience difficult without knowledge of the exact flavors of the wine inside a bottle to be purchased.

SUMMARY

In some aspects, a computing device implemented method comprises receiving data representing features of a first wine and data representing features of a second wine collected by processing one or more signals representing light scattered light from a bottle containing the first wine and a bottle containing the second wine, receiving survey-based data representing the similarity between the first and second wines, and training a machine learning system using the features of the first wine, the features of the second wine and the survey-based data that represents the similarity between the first and second wines.

In some implementations, a method of illuminating and extracting scattered and transmitted light from a liquid within a sealed glass bottle includes initiating transmission of an incident light beam from a light source to the sealed bottle, directing the incident light beam to totally internally refract within a wall of the sealed bottle and thereby cause an evanescent wave within the liquid to generate scattered or absorbed light, receiving the scattered or absorbed light from the liquid contained in the sealed bottle, and processing one or more signals representative of the scattered or absorbed light, the signals indicative of one or more molecules indicative of a characteristic being present in the liquid contained in the sealed bottle.

In some instances, the method includes one or more of the following: directing the light beam to totally internally reflect comprises directing the light beam to transmit through a prism in contact with the bottle wall. Receiving the scattered or absorbed light comprises directing the scattered or absorbed light through toward a spectrometer via a second prism. Placing an index-matching material between the prism and wall of the bottle. Directing the light beam to totally internally reflect comprises directing the light beam to transmit through a ball lens in contact with the bottle wall. Receiving the scattered or absorbed light comprises directing the scattered or absorbed light through optics toward a spectrometer.

In some implementations, a method of illuminating and extracting scattered and transmitted light from a liquid within a sealed glass bottle includes initiating transmission of an incident light beam from a light source to the sealed bottle and generate scattered or absorbed light, separating a signal representative of light scattered or absorbed by the glass bottle and a signal representative of light scattered or absorbed by the liquid, receiving the signal representative of light scattered or absorbed by the liquid, and, processing the signal representative of light scattered or absorbed by the liquid, the signal indicative of one or more molecules indicative of a characteristic being present in the liquid contained in the sealed bottle.

In some instances, the method includes one or more of the following: separating the signals comprises directing the signal representative of light scattered or absorbed by the glass bottle and the signal representative of light scattered or absorbed by the liquid through a lens to generate two spatially-separated signals. Separating the signals comprises blocking the signal representative of light scattered or absorbed by the glass bottle from being received at a spectrometer.

In some implementations, a computing device implemented method includes receiving data representing features of a first wine and data representing features of a second wine collected by processing one or more signals representative of light scattered light from a bottle containing the first wine and a bottle containing the second wine, receiving survey-based data representing a similarity between the first and second wines, and training a machine learning system using the features of the first wine, the features of the second wine and the survey-based data that represents the similarity between the first and second wines.

In some instances, the method includes one or more of the following: storing the data in a wine library, wherein the library is a distributed database of records of wine data. Storing the data in a wine library entry, wherein the features include descriptive attributes of wine including the concentration of one or more molecules of interest present in the wine, and the library entry includes identifying features of the bottle.

In some implementations, a system for illuminating and extracting scattered and transmitted light from a liquid within a sealed glass bottle includes a light source configured to allow initiation of transmission of an incident light beam to the sealed bottle, a light-redirecting object configured to direct the incident light beam to totally internally refract within a wall of the sealed bottle and thereby cause an evanescent wave within the liquid to generate scattered or absorbed light, a spectrometer configured to receive the scattered or absorbed light from the liquid contained in the sealed bottle, and a processor configured to process one or more signals representative of the scattered or absorbed light, the signals indicative of one or more molecules indicative of a characteristic being present in the liquid contained in the sealed bottle.

DETAILED DESCRIPTION

Figure 1:
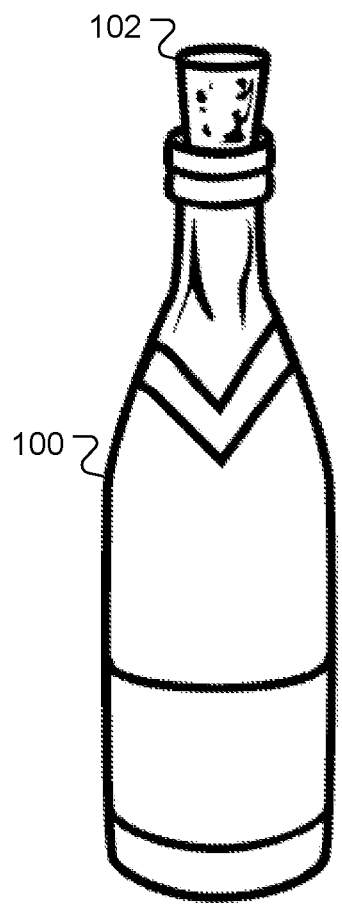
FIG. 1 illustrates a bottle of wine.

Referring to FIG. 1, a bottle of wine 100 is illustrated that has the general size and shape of many commercially available bottles. The wine bottle 100 may be made of glass. While one particular bottle is illustrated in the figures, other bottles of similar or different size, shape, and style may be utilized. Further, in some arrangements, other types of containers, vessels, etc. may be utilized, e.g., vessels for the storage or delivery of wine.

A wide range of wines with differing flavors and prices are currently available to consumers. Wine is a complex beverage, with many different molecules present in a typical bottle of wine. The complexity of wine leads to many different types of wine and differing flavor profiles due to the particular mix of molecules in each bottle. This mix of molecules changes between bottles, and also within a bottle as a particular bottle of wine ages. It is estimated that there are up to one thousand different molecules in wine, with most of these molecules having a similar chemical composition, and being present in very low concentrations. It would be advantageous to detect exactly which molecules in which quantities are present in the wine bottle 100, e.g., before the wine bottle 100 is opened by removing closure 102 or before it is purchased. Several applications for detecting and cataloguing the contents of an unopened bottle of wine are described.

Figure 2:
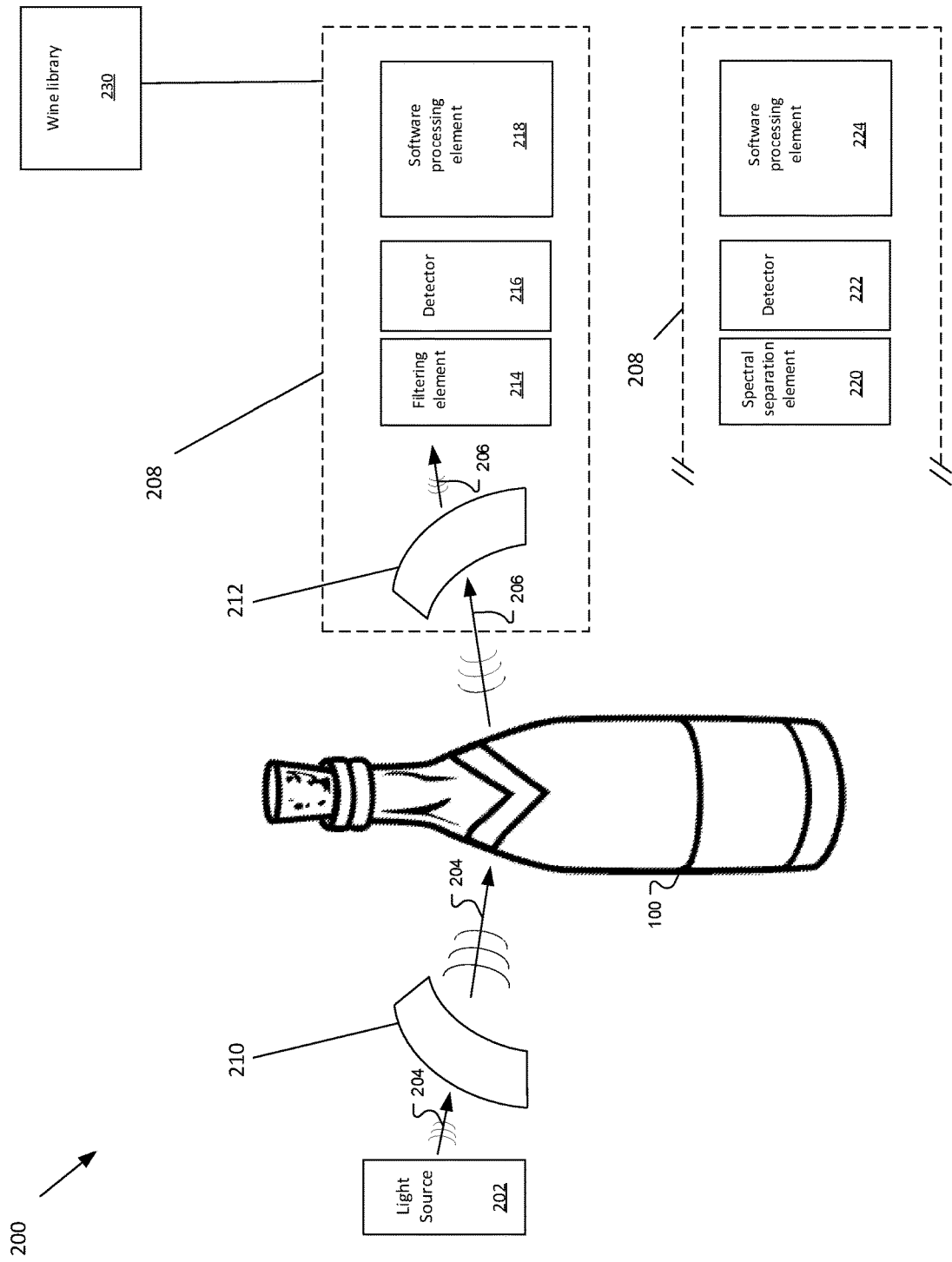
FIG. 2 illustrates a system incorporated into a device for detecting characteristics of the wine within the bottle of FIG. 1.

Referring to FIG. 2, a device is illustrated that is capable of detecting wine characteristics. One or more techniques may be employed to detect wine molecules in a non-invasive manner, e.g., without opening the wine bottle 100. For example, a spectroscopic system may be employed to detect the presence of molecules such as certain molecules of interest.

In this spectroscopic arrangement, the detection system is incorporated into a device 200, which is easily portable and either includes or can be adapted to include data collection, processing, and presentation needs. The device 200 includes a light source 202 that emits light (sometimes referred to as incident light 204) into the bottle 100. In some implementations, the light source is a laser. In some implementations, the light source is an LED, such as a broadband LED. The incident light 204 may pass through an optical sampling/filtering element 210 before it is incident on the bottle 100. The incident light 204 interacts with the contents of the bottle and is scattered in an omnidirectional manner. The scattered light 206 can contain faint "optical fingerprints" of the different molecules present in the wine. The "optical fingerprints" correspond to peaks or dips where the scattered light 206 has been scattered or absorbed by particular molecules. In this way, the term "scattered light" 206 emerging from the bottle 100 may include light that is transmitted, reflected, refracted, and dispersed, and constitutes light that has been scattered or absorbed and emitted on an atomic/molecular level due to the liquid in the bottle 100.

In this arrangement, the device 200 includes a detection system 208 that is capable of collecting the scattered light 206. The detection system 208 may include an optical collection element 212 that the scattered light 206 passes through before being incident on the detection system 208. The detection system 208 can include a filtering element 214 (e.g., one or more optical filters, diffraction grating, etc.), a detector 216 (e.g., a charge-coupled device (CCD) detector or a photodiode), and a software processing element 218 (e.g., software, hardware, or a combination of software and hardware). The information carried by the scattered light 206 is provided to the software processing element 218, which processes the collected information and determines, for example whether the wine contained in the bottle 100 is tainted or not. In some implementations, the information determined by the software processing element 218 can be stored in a database or wine library 230.

In some implementations, the scattered light 206 can go through one or more pre-processing steps before the information carried by the scattered light 206 is provided to the software processing element 218. For example, the filtering element 214 can include a bandpass filter that isolates one of the "optical fingerprints" that corresponds to a peaks or dip where the scattered light 206 has been scattered or absorbed by a particular molecule. The filtering element 214 can also include one or more other filters for filtering unwanted signals apart from the peaks or dips of the molecule of interest, such as Rayleigh scattered light, unwanted fluorescence, etc. Following filtering by the filtering element 214, the scattered light 206 is directed onto a surface of the detector 216. In such an implementation, the detector 216 can be a photodiode which provides an output to the software processing element 218 that indicates the presence of molecules of interest (such as tri-chloroanisole or TCA molecules) in the wine contained in the bottle. The software processing element 218 can then compare the output of the detector 216 to a threshold value to determine whether a signal is present.

In some implementations, the detection system 208 includes a spectral separation element 220, a detector 222, and a software processing element 224. The scattered light 206 goes through one or more pre-processing steps before the information carried by the scattered light 206 is provided to the software processing element 224 (e.g., a different software processing element than the software processing element 218 described above). That is, the scattered light 206 is primarily processed by the software processing element 224 to remove unwanted signals apart from the peaks or dips of interest. In such an implementation, the spectral separation element 220, which can be a diffraction grating, is configured to spectrally separate the scattered light 206. Following spectral separation by the diffraction grating, the scattered light 206 is directed onto a surface of the detector 222 (e.g., a different detector than the detector 216 described above). In such an implementation, the detector 222 can be a CCD detector. The detector 222 then provides an output to the software processing element 224, which processes the output to determine whether a signal of interest is present in the scattered light 206.

In some implementations, the diffraction grating can be replaced with or enhanced by the presence of an optical cavity in a Raman-type process to selectively detect compounds or enhance the signal.

In some implementations, the filtering elements 214 can be implemented either in hardware or in software. More than one type of filtering scheme can be used, or combined such that the filtering is distributed between one or more of the filtering schemes. In some implementations, the different filtering schemes can be used in concert or as backup systems for each other.

One or more mechanical implementations may be designed to interface the light source 202, the optical sampling/filtering element 210, and/or the detection system 208 to the bottle 100. For example, one or more mechanical clamps and/or structures that conform to the bottle's shape may be used to appropriately position the system components such that they can interact with the bottle's 100 contents. In one arrangement, a housing structure may provide an interface between the device 200 and the bottle 100 (e.g., the housing clamps or slides over the bottle). In another arrangement, the device 200 is designed to fit around the bottle (e.g., in a "donut" configuration). As discussed further below, the incident light may be coupled to the wine bottle by means of a coupling element (e.g. a prism or a ball lens) connected to the bottle by a refractive index matching element (e.g. a gel or an optically transparent polymer). Alternatively, the light may be coupled directly into the bottle in a straight path. In either configuration, the light is coupled to a wall of the bottle to cause total internal reflection (Brewster's angle) within the bottle wall, such that an evanescent field leaks into the wine at the wine-glass interface.

Various processing techniques may be employed by the detection system 208 in order to collect and process the information needed to determine characteristics of the wine. For example, as described above, one or more filtering operations may be executed on the scattered light 206, on one or more signals produced from the scattered light 206 by the detection system 208, or on a combination of the scattered light 206 and the corresponding signal(s), etc. Through particular filtering operations (e.g., selecting appropriate frequency ranges), the fingerprint of the molecule of interest may be detected in the wine.

Parameters of the incident light 204 and the light source 202 may be selected based upon an interaction of the incident light 204 with the bottle 100 and its contents. In general, when the incident light 204 interacts with the molecules contained in the wine, the light may be absorbed (and later re-emitted) or the light may be scattered. The former process forms the basis of the measurement technique known as absorption spectroscopy, while the latter process forms the basis for the measurement technique known as Raman spectroscopy. Either of these techniques, or variations thereof, may be applied to the detection of molecules of interest.

For molecules, two types of scattering may occur. The first type of scattering, Rayleigh scattering, is an "elastic scattering" process in which a photon bounces off a molecule like a billiard ball, emerging with the same energy as it entered. The second type of scattering, Raman scattering, is an inelastic scattering process in which the light scattered by a molecule emerges having an energy level that is slightly different (more or less) than the incident light. This energy difference is generally dependent on the chemical structure of the molecules involved in the scattering process.

Typically, most scattering that occurs in nature is Rayleigh scattering. For example, Rayleigh scattering provides the blue color to the sky: the intensity of the light that gets Rayleigh scattered by a molecule is inversely proportional to the fourth power of the wavelength of the incident light, which means that blue light (shorter wavelength) is scattered 10 times more than red light (longer wavelength), and hence sunlight incident on gas molecules in the air gets scattered as blue light in every direction. Comparatively, Raman scattering is less prevalent. For approximately one million photons Rayleigh scattered by a molecule, only one or a few photons are Raman scattered. Therefore, the most significant challenge in Raman spectroscopy is to separate the Raman scattered light from the predominant Rayleigh scattering that accompanies it. The comparative scarcity of Raman scattering also means that it can be considered more difficult to detect than Rayleigh scattering.

Raman spectroscopy is based on the fact that different molecular vibrations within a sample translate into bigger or smaller shifts in frequency for any Raman scattered light, and because this vibrational information is specific to the chemical bonds and symmetry of the molecules, the frequency shifts translate into a specific molecular structure. Thus, Raman spectroscopy can be considered as a powerful investigative tool capable of providing "optical fingerprints" by which molecules can be identified, for example TCA, methanethiol, etc.

More technically speaking, a Raman scattering event can proceed as follows. An incoming photon interacts with a molecule and polarizes the cloud of electrons around the nuclei, exciting the molecule to a virtual energy state (i.e., not one of the molecule's real excited states, but a state created by the photon-induced polarization, whose energy is determined by the frequency of the incident photon). This state is not stable and the photon is quickly re-radiated, or scattered. If nuclear motion is induced during the scattering process, energy will be transferred either from the incident photon to the molecule or from the molecule to the scattered photon. The process is inelastic, and the energy of the scattered photon will differ from that of the incident photon by one vibrational unit. Because the vibrational states of the molecule are dictated by its chemical structure, the shift in energy of the scattered photon will likewise then contain information about that chemical structure. If nuclear motion is not induced and only electron cloud distortion is involved in the process, then the photon will be scattered with only a negligible change in frequency as electrons are comparatively light. This (nearly) elastic scattering process is Rayleigh scattering.

Different molecules are made up of different atoms in different configurations, so each molecule bends, stretches, and vibrates in a slightly different way. Some of the photons scattered by a molecule will change the way the molecule is vibrating, and in turn, the energy of those photons will be changed by a very small amount. This change in energy is directly proportional to the vibration of the molecule, and hence to its chemical configuration, so Raman scattered light can be thought of as an "optical fingerprint" that can be used to identify a molecule by its chemical structure. Other spectroscopic techniques may be used to investigate molecules, and could be used to detect molecules of interest with practically the same components as necessary for Raman spectroscopy.

One measurement example is the technique of absorption spectroscopy. Absorption of light by molecules occurs at frequencies that are dictated by their chemical structure. More specifically, absorption occurs at wavelengths that match one of the electronic, rotational, or vibrational transitions of a molecule. Hence a dip in transmission at a given wavelength indicates the presence of a molecular transition at that wavelength. Because electronic, rotational, and vibrational transitions are particular to the chemical structure and symmetry of a molecule, the various dips in transmission recorded can be used to determine the presence of a given molecule. The dips in transmission observed in absorption spectroscopy are analogous to the shifts in frequency observed in Raman spectroscopy, and they too can be seen as "optical fingerprints" by which molecules can be identified (in fact the absorption spectrum and the Raman spectrum of a given molecule often resemble each other quite closely).

One key difference between the two techniques is that in absorption spectroscopy, the illuminating light source has to be tuned to excite the transition frequencies of the bonds or groups that vibrate for the molecule in question, whereas in Raman spectroscopy, the illuminating laser can be tuned to an arbitrary virtual energy state. Another example of a technique that can be used to investigate molecules is laser induced breakdown spectroscopy. In this technique, a pulsed laser is focused to a small spot within a sample. This highly energetic laser pulse forms a plasma in its focus, atomizing the molecules therein. As the plasma cools, excited atoms in the plasma emit light of characteristic wavelengths distinctive to the plasma. This light contains the "optical fingerprint" of the elements contained in the molecules ablated by the laser pulse, and can therefore also be used to investigate their chemical structure.

In implementations in which Raman spectroscopy is employed, a spectrometer can include a light source, a sampling apparatus, and a detector. In the illustrated example, equivalent functionality is provided by the light source 202, the optical sampling/filtering element 210, and the detection system 208, individually or in concert (based upon the design). From a functional perspective, the light source 202 (e.g., a laser or an LED source) provides incident light for the molecules to scatter, and the detection system 208 collects, spectrally separates and/or filters the scattered light and measures the signal. While this functionality may be common to numerous Raman spectrometers, the design of the individual components (e.g., light source, detection system) may vary based upon system and component parameters (e.g., operating wavelength, detector sensitivity, spectrograph used to separate the scattered light, physical footprint, etc.).

One or more system and component parameters, features, etc. may be defined for spectroscopic analysis and detection of molecules present in the wine bottle 100. For example, a relatively long wavelength may be chosen for the light source 202 such that the tinted glass (e.g., of the wine bottle 100) and the pigments in the wine are practically "invisible" to the incident light. In one arrangement, a 1064 nm laser may be employed to perform Raman spectroscopy. Other laser wavelengths are also possible, e.g., 975 nm or 1030 nm. Lasers of this type are generally considered advantageous for Raman spectroscopy because they allow for substantial suppression of unwanted background absorption and fluorescence (absorbed and re-emitted light from molecules other than the molecules of interest) that can accompany and overwhelm the desired Raman scattered light. In the particular application of TCA detection in bottles of wine (described in detail below), most of the unwanted background absorption and fluorescence can come from the tinted glass bottle and the pigments in the wine. The laser used can be a continuous or pulsed laser, for example an NdYag (Neodymium-doped Yttrium Aluminum Garnet) laser.

In one implementation, the light source 202 can be a continuous-wave diode-pumped solid-state laser with a wavelength of 1064 nm and a maximal output power of 3.5 watts. The power of the laser is chosen so as to maximize the signal obtained from the desired molecule in the bottle of wine. The strength of the signal from a particular molecule is proportional to its concentration in the wine as well as to the power of the laser exciting the Raman transition that gives rise to this signal. Hence, a laser with a higher power leads to a stronger signal (if there are more photons impinging on the molecule per unit time, there will be more Raman scattered photons detected per unit time, and hence a stronger signal). For detecting wine molecules, various types of detectors may be employed. For example, a germanium photodiode detector that is sensitive in the spectral fingerprint region of organic molecules may be used in the detection system 208. This fingerprint region can be considered to reside in the near-infrared (NIR) mid-infrared (MIR) frequency range, with the Raman frequency shifts located between 400 and 4000 cm−1 from the excitation wavelength. This fingerprint region can also be considered as including Raman scattered light with a wavelength range (rather than shift) of e.g., 1.11 to 1.85 µm. For example, the detector 216 or 222 can be a germanium photodiode sensitive in the near infrared region between 700 and 1800 nm from Thorlabs GmbH. Its power range is from 5 nW to 500 mW, and it has a resolution of 1 nW. This wide range in sensitivities allows the photodiode both to detect the Raman scattered light and to align the optical components in the device. The photodiode is read out by the PM100USB console, also from Thorlabs. This console allows computer control of the attached sensor and can be used with several different detectors.

In some implementations, the photodiode can be replaced by two photodiodes, one which is sensitive at powers below 1 nW and has a higher resolution, to be used for detection, and a second one which is sensitive at powers up to 3 W, to be used for alignment.

In some implementations, the detector can be TE-cooled indium gallium arsenide (InGaAs) detector.

Along with different detector types, detection parameters may be defined and adjusted for the application. For example, to provide the requisite level of sensitivity, an appropriate signal-to-noise ratio may be needed and provided through one or more procedures, such as the suppression of unwanted light (e.g., stray light from the light source 202, noisy ambient light, Rayleigh scattered light, background fluorescence, etc.). Following suppression of unwanted light and spectral separation by a spectrograph, the obtained signal will consist of the total Raman spectrum of all the molecules contained in the bottle of wine. Further techniques may be employed in order to isolate and distinguish the Raman signal of a molecule of interest from the Raman signal of other molecules contained in this spectrum. In one arrangement, the Raman spectra of unwanted molecules within the total spectrum may be identified by previous knowledge of these spectra (e.g., by previous tabulation, measurement, etc.) after spectral separation by a spectrograph and removed (e.g., by vector subtraction). The requisite previous knowledge can be incorporated into the software processing operations of the software processing element 224 of the detection system 208.

As described above, in another arrangement, optical filters remove all but part of the desired Raman spectrum from the total obtained signal before it is detected, without the need for spectral separation. In this arrangement, it may be possible to use a photodiode as the detector 216 instead of a CCD. The spectra of unwanted reflections from the wine bottle (e.g., at the air/bottle interface, the bottle/wine interface, etc.) can also be characterized (e.g., estimated, measured, etc.) and included in one or more pre-processing and/or processing operations (e.g., before information carried by the scattered light 206 is provided to the software processing element 218). Such pre-processing and/or processing operations can include removal of the unwanted spectra, such as subtraction of the glass spectrum from the glass-and-wine spectrum.

To identify the desired spectrum for the molecule of interest, one or more techniques can be employed, e.g., optical and/or signal filtering, amplifying, etc. To manipulate the incident light 204 and the scattered light 206 preceding the acquisition of this spectrum, different design parameters may be employed. In one arrangement, the scattered light 206 scattered by the contents of the bottle may be collected along the same path as the incident light (e.g., in the backwards direction in a monostatic manner) by means of a dichroic mirror that is capable of separating the scattered light 206 from the incident light 204 and redirecting the scattered light 206 along a different path than the incident light 204, or by means of a carefully chosen geometric arrangement of the incident light and the detector(s) such that the scattered light is separated from the incident light. In another arrangement, the scattered light may be collected on the same axis as the incident light 204, but on the other side of the bottle 100 (i.e., in the forward direction in a bistatic manner). In another arrangement, the scattered light 206 may be collected in the forward direction, the backward direction, and at a range of angles in between. Such an arrangement can maximize the strength of the collected signal, because molecules scatter light over a solid angle of $4\pi$. Such an arrangement can also minimize the light absorbed by the wine (e.g., light that is scattered and re-scattered until it is lost in the medium). Such an arrangement can be accomplished by using multiple detectors 216, 222 positioned at various points along the perimeter of the bottle 100.

In the illustrated example, light producing hardware (e.g. the light source 202 and the optical sampling/filtering element 210) and light collecting hardware (e.g., the detection system 208) are incorporated into a single device. However, one or more other types of devices, platforms, etc. may be utilized to provide the molecule of interest detection functionality.

In one arrangement, a Raman spectrometer may be used for making wine characterization measurements. Generally, such a spectrometer includes the light source 202 such as a laser or LED source, the optical sampling/filtering element 210, and the detection system 208. One or more types of lasers or LED may be used operable at a wavelength in the infrared spectral region (e.g., at approximately 1064 nanometers (nm), 940 nm, 975 nm, 1030 nm, 1120 nm, 1320 nm, 1440 nm, etc.)). By operating in this spectral region, unwanted absorption and fluorescence from the wine bottle and the pigments of the contained wine can be substantially suppressed. Operating power may range from less than 500 milliwatts (mW) or even less than 100 or 50 mW to more than one watt. In general, the strength of the signal scattered by a particular type of molecule is proportional to its concentration as well as to the laser power exciting the Raman transition that produces the signal. In other words, if more photons are impinging upon the molecule per unit time, more Raman scattered photons will generally be detected per unit time, thereby producing a relatively larger signal. In some arrangements, light source parameters are defined to minimize health and safety concerns. For example, the light source and associated optics may be placed in protective housing to reduce or prevent the probability of harming a user's eyes. In some implementations, the power of the light source may be set to operate at a level that reduces the probability of harming a user's eyes (e.g., by reducing or blocking off the intensity of any specular reflections).

The detection system 208 may include one or more optical collection elements 212, one or more filtering elements 214 and/or spectral separation elements 220 (e.g., one or more optical filters such as a bandpass filter or a dichroic filter, a diffraction grating such as a volume phase holographic transmission grating, etc.), various other optical components such as optical fibers, lenses, mirrors, fiber-based dispersive elements (e.g. fiber Bragg gratings), and one or more detectors 216, 222 (e.g., one or more charge-coupled device (CCD) detectors, photodiodes, etc.), and one or more software processing elements 218, 224. Normally, the type of spectrograph used in dispersive Raman spectroscopy is a surface-relief reflective diffraction grating or a transmissive grating such as a volume phase holographic transmission grating (VPHTG). Absorption spectroscopy uses a modified spectrograph of this type called a monochromator, which also contains a diffraction grating, or increasingly, a technique called Fourier Transform spectroscopy (FTIR if in the infrared), which uses a type of Michelson-Morley interferometer. A diffraction grating can be considered as an optical component with a periodic structure that splits and diffracts light into beams of different wavelengths. Such a periodic structure can for instance be a repeating pattern of relatively small grooves or ridges etched onto a surface at regularly spaced intervals. Diffraction gratings can be either transmissive or reflective and can modulate the phase rather than the amplitude of the incident light 204. An alternative to groove-based surface-relief diffraction gratings are volume phase holographic transmission gratings (VPHTGs). VPHGTs do not have physical grooves; instead, they contain an optically thick but transmissive dichroic gelatin film which has a periodic hardness and is positioned between layers (e.g., two) of clear glass or pure silica. The periodic hardness of the gelatin translates into a periodic refractive index which then modulates the light in a manner similar to a surface-relief pattern. VPHTGs are generally more efficient and produce less unwanted scattering.

Along with the various types of detectors that may be employed, various electronic components and other associated modules may be included with the detector to provide additional functionality. For example, data from the detector is typically read and interpreted by the software processing element 218, 224 (e.g., processed by software, hardware, or a combination of software and hardware associated with a computing device). The software processing element 218, 224 may have other functions. For example, one or more user interfaces may be provided for operational control, data acquisition, data presentation, etc.

In implementations in which the scattered light 206 is filtered by the filtering element 214 (e.g., a bandpass filter) and directed onto the surface of the detector 216 (e.g., a photodiode), the software processing element 218 compares an output of the detector 216 to a threshold value to determine whether a signal for a molecule of interest is present.

In implementations in which a Raman spectrometer is used, the scattered light 206 is spectrally separated by the spectral separation element 220 (e.g., a diffraction grating) and directed onto the surface of the detector 222 (e.g., a CCD detector), the software processing element 224 processes the signal from the scattered light 206 to remove unwanted signals apart from the signals for the molecules of interest. The Raman spectrometer generally includes a laser as the light source 202.

Depending on the implementation, various components may be used as the light source 202. For example, several high powered LEDs or a laser in the requisite near infrared region can be used.

The spectral width of such LEDs is not as narrow as that of a laser, but an additional filter may be used to narrow the spectral width. Various devices may also be used as the detector 216, 222 in the detection system 208. For example, one or more types of photodiode (e.g., avalanche photodiodes) may be used to detect the scattered light.

Different light collection techniques may be used by the detector 216. For example, the detector 216 may employ one of several filtering techniques (e.g., bandpass filters, dichroic filters, etc.) to isolate particular spectral regions (e.g., frequencies, frequency bands, etc.) having particular spectral widths. In one arrangement, a narrow bandpass filter may be used to isolate one or more of the frequency peaks associated with the signal of a molecule of interest. By focusing upon single frequencies (and not broader spectra), a single signal characteristic such as amplitude may be used to ascertain the presence of the molecule of interest (e.g., by applying one or more predetermined thresholds). In this way, the presence or absence of the molecule of interest may be determined without the need to detect, spectrally separate, and characterize the total spectrum obtained from the bottle of wine (the combined spectrum of all the molecules present within it). In such an arrangement, a spectral separation element 220 such as a spectrograph is not needed, and previous knowledge of the spectra of unwanted molecules does not need to be included in the software processing element 218.

In some implementations, filtering element 214 includes two or three different filters (e.g., optical filter). The first filter may be a bandpass filter that is used to eliminate spectral noise from the incident light by blocking the transmission of substantially all but a narrow band of frequencies around a central frequency of interest which is wholly transmitted. This first filter narrows the light and eliminates unwanted frequencies (e.g., the carrier frequency). In implementations where the light source 202 is an LED (e.g., a diffuse light source) this first filter can be used, and in implementations where light source 202 is a laser with a narrow spectral linewidth this first filter can be omitted.

A second filter (e.g., optical filter) that is part of filtering element 214 can be a longpass edge filter, a notch filter, etc., and is used to suppress the unwanted Rayleigh scattered light that accompanies the Raman scattered light of interest. Longpass edge filters work by blocking transmission below a given frequency, and allowing transmission above it. Notch filters work by allowing the transmission of all but a very narrow band of frequencies around a central frequency that is wholly suppressed.

The third filter (e.g., optical filter) that is part of filtering element 214 can be a very narrow bandpass filter used to isolate the Raman scattered light of interest (e.g., for a particular molecule such as TCA, methanethiol, etc.) from the rest of the light scattered by the sample. This filter is picked such that its central wavelength matches the frequency of the Raman scattered light of interest. To isolate Raman scattered light from the molecule of interest the filter can be selected to isolate both the wavelength of particular molecule of interest as well as which of the given molecule's Raman shifts are isolated.

It is also possible to do a multi-component analysis where select Raman peaks of several molecules could be isolated. Such multi-component analysis can include chemometrics (the use of mathematical and statistical methods for extracting information from chemical systems and correlating quality parameters or physical properties to analytical instrument data). These techniques can include principal component analysis (PCA), log-ratio analysis (LRA), etc. and can de-convolute the total signal. In some instances, machine learning techniques can also be used to understand wine (e.g., identify a particular wine).

To change which molecule of interest (or particular Raman shift for a molecule of interest) device 100 is detecting, the third filter used can be quickly and easily substituted for a different third filter having a different filtering capability specific to the new application.

These filters are easily interchangeable thin film disks about an inch in diameter which are available off the shelf in a variety of central wavelengths but which can also be custom made to fit a desired wavelength. As an example, the filters which make up filtering element 214 can be made by Thorlabs GmbH.

One or more techniques may be employed to investigate specific frequencies, relatively narrow frequency bands, etc.

The functional steps or detecting wine molecules can be generally grouped into four main parts: illumination, optical processing, detection, and software processing. More specifically, a complete measurement includes initiating illumination, expanding and/or directing the illuminating light into the bottle using optical components, filtering the scattered light or signals, detecting the filtered light, processing the detected signal by software which consists of recording the power incident on the photodiode and determining whether it is above a predetermined threshold level. Finally, the result can be displayed on a graphical user interface (GUI). In some implementations, the software not only controls device 200 function and initiates measurement, but also enables storage and transmission of the obtained data.

Figure 3:
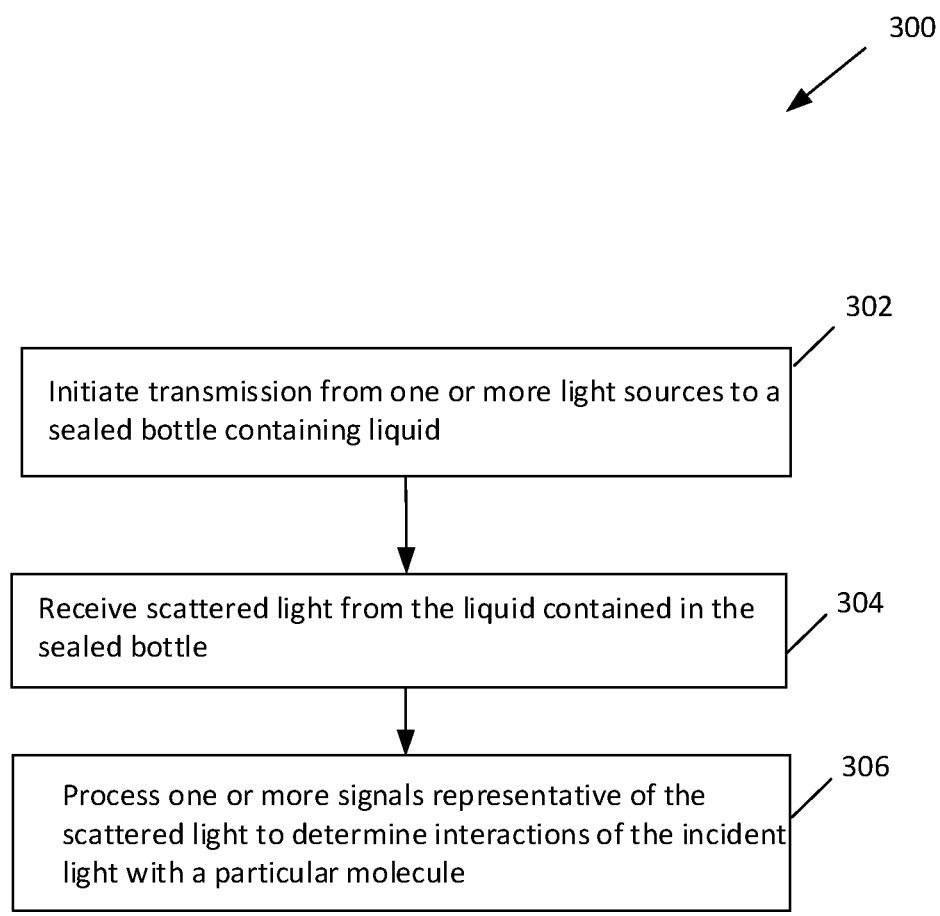
FIG. 3 is an example flow chart of operations for detecting wine characteristics.

Referring to FIG. 3, a flowchart 300 illustrates the operations of the liquid fault detection system (e.g., the light source 202, the optical sampling/filtering element 210 and the detection system 208 shown in FIG. 2). Operations of the fault detection system are typically executed by a single device (e.g., the device 200). However, operations may also be executed by multiple devices. Along with being executed at a single site (e.g., the location of a wine bottle), the execution of operations may be distributed among two or more locations. In some arrangements, a portion of the operations may be executed at a central location (e.g., a wine data center or similar facility).

Operations of the liquid fault detection system may include initiating 302 transmissions of incident light from one or more light sources to a sealed bottle containing liquid. For example, a wine bottle (e.g. the wine bottle 100) may be illuminated as initiated by a light source incorporated into a device (e.g., a laser, LED, etc. provided by the light source 202 of the device 200). Operations also include receiving 304 scattered light from the liquid contained in the sealed bottle. For example, scattered light from the bottle and the liquid content of the bottle may be received by a detector incorporated into the device (e.g., the detector 216, 222 of the detection system 208). Operations can also include processing 306 one or more signals representative of the scattered light to detect interactions of the incident light with a particular molecule present in the contained liquid. The scattered light may be filtered prior to processing one or more signals representative of the scattered light. The scattered light may also be filtered prior to being received (e.g., by a detector such as the filtering element 214, which can be a bandpass filter that isolates one of the peaks in the desired molecule frequency spectrum). The scattered light may also be filtered as part of the processing. In this way, processing one or more signals representative of the scattered light includes filtering the signals. Alternatively, the scattered light may be spectrally separated (e.g., by the spectral separation element 220) prior to processing one or more signals representative of the scattered light, and the scattered light may be filtered subsequent to being received by a detector (e.g., by subtracting unwanted signals from the total obtained spectrum with the software processing element 218, 224). By blocking or subtracting unwanted light signals in this way, a representative measure of the amount of molecule of interest present in the contained wine may be produced.

Detecting Defective Wine

Some of the molecules present within the wine bottle 100 can be wine faults or defects that can cause unpleasant olfactory and gustatory characteristics and may result from a variety of sources, such as poor hygiene at the winery, excessive and/or insufficient exposure of the wine to oxygen, excessive or insufficient exposure of the wine to sulfur, overextended maceration of the wine either pre- or post-fermentation, faulty fining, filtering and stabilization of the wine, the use of dirty oak barrels, overextended barrel aging, the use of poor quality corks, etc. External to a winery, other factors associated with a wholesaler, retailer, end user, etc. can contribute to faults in a bottle of wine. These include poor storage and/or transport, in which the wine is e.g., exposed to excessive heat and/or temperature fluctuations.

Using the device 200, a purchaser can determine whether a bottle should be returned or possibly not purchased in the first place, without the need to open the bottle. A producer can also keep back tainted bottles, guaranteeing production of taint-free wine, and a supplier can filter the wine they buy and resell. The system can also suppress the occurrence of embarrassing events both in restaurants and in private (e.g., serving tainted wine to friends, feeling intimidated by a sommelier etc.).

"Cork taint" is a term used in the wine industry to describe one such wine fault, whose defining characteristics are a set of undesirable smells and tastes in a bottle of wine. Severely corked wine can be undrinkable. In general, cork taint can be detected after the bottling and opening of a bottle of wine. Several factors can contribute to the presence of cork taint, amongst them contaminated wooden barrels, storage and transport conditions, cleaning products in a winery, contaminated machinery or bottling equipment, airborne molds etc. In some instances, a cork stopper used to seal the bottle may be responsible. It is from this process that the term "corked" has evolved to describe wine tainted in this way. Not only does this lead to unhappy customers, but it also increases transactional costs due to the corrective action required upon detecting a "corked" bottle of wine (e.g., removing the tainted bottle from the supply chain, returning the bottle to the wine retailer, etc.)

The 2,4,6-trichloroanisole (TCA) molecule is the primary cause of cork taint in a bottle of wine. Wine taint is also caused by 2,4,6-tribromoanisole (TBA) molecules, but the TBA molecule is generally less prevalent than TCA. Sulfur taint is also undesirable, and is caused by compounds like mercaptans/thiols such as ethyl mercaptan or methanethiol. The TCA molecule is typically transferred to the wine from the cork stopper, but it may also come from other sources, and introduced either by the cork or before bottling. In general, wine containing TCA has a characteristic odor, predominantly described as resembling the scent of a moldy substance. In addition to wine, TCA can also be found in bottled water, other types of alcohol such as beer, spirits, soft drinks, and other food products.

Molecules of interest like TCA and methanethiol contain distinctive chemical bonds that distinguish them from the rest of the molecules in wine, and which yield characteristic spectroscopic signals (e.g., Raman frequency shifts) that are unique to these molecules. In the case of TCA, this is due to the presence of a carbon-chlorine bond, and in the case of methanethiol, this is due to the presence of a carbon-sulfur bond.

TCA may be produced as a result of the interaction between microbes and chlorinated phenolic compounds present in natural cork (more specifically, these microbes convert chlorophenols into chlorinated anisole derivatives, which are then present in the cork and dissolve into the wine), but they can also arise in the absence of microbes. The chlorophenols can be absorbed by cork trees from contaminants in pesticides and wood preservatives. Further, chlorophenols can be a product of the chlorine bleaching process used to sterilize or bleach, wood, cork, and paper, or they can migrate from other objects, such as shipping pallets that have been treated by chlorophenols. The microbes that produce TCA can be mold-forming fungi that live in small pores in the bark of cork trees, airborne fungi in the facility, and bacteria or fungi like *Aspergillus* spores, *Penicillium* spores, Actinomycetes, *Botrytis cinerea, Rhizobium spores, Streptomyces*, etc.

Referring again to FIG. 3, operations to detect the presence of a particular molecule of interest (e.g., TCA or methanethiol) can include processing 306 one or more signals representative of the scattered light to detect interactions of the incident light with the particular molecule. The scattered light may be filtered prior to processing one or more signals representative of the scattered light. The scattered light may also be filtered prior to being received (e.g., by a detector such as the filtering element 214, which can be a bandpass filter that isolates one of the peaks in the TCA frequency spectrum). The scattered light may also be filtered as part of the processing. In this way, processing one or more signals representative of the scattered light includes filtering the signals. Alternatively, the scattered light may be spectrally separated (e.g., by the spectral separation element 220) prior to processing one or more signals representative of the scattered light, and the scattered light may be filtered subsequent to being received by a detector (e.g., by subtracting unwanted signals from the total obtained spectrum with the software processing element 218, 224). By blocking or subtracting unwanted light signals in this way, a representative measure of the amount of TCA present in the contained wine may be produced.

The method described herein that investigate single molecular of interest (such as TCA) is similar to those used in Raman spectrometers, but with differences in the filtering and signal processing. In a traditional Raman spectrometer the scattered light is optically filtered to remove the unwanted Rayleigh scattered light that accompanies the Raman scattered light of interest, and the incident light can be optically filtered to eliminate spectral noise that is not at the wavelength of interest. This is also done in device 200. However, in a Raman spectrometer, the key step in a measurement is the spectral separation of the scattered light into all of its constituent frequencies. The resulting spectrum contains the "optical fingerprints" of all the different molecules contained in the sample, is analyzed by software, and molecules are identified by comparison with a database of known molecular spectra. These two key steps in a Raman spectrometer—spectral separation and analysis by software—can be sidestepped completely in device 200. In device 200, the scattered light is instead optically filtered a second time to remove all but the light at one particular frequency. This key step in device 200 does not take place in a conventional Raman spectrometer, and allows the software processing to be reduced to a simple threshold measurement. Device 200 is simplified both in terms of hardware and software.

Raman spectrometers typically extract a full spectrum for analysis to determine the composition of a sample or to identify one of several substances in a sample. The device 200 can be configured in this manner is configured to determine a small number of predetermined molecules of interest in a sample, (e.g., TCA and methanethiol) it is not necessary to spectrally separate the scattered light and analyze the total spectrum obtained. It suffices to look for the presence of scattered light with a frequency corresponding to one of the Raman frequency shifts of the molecule of interest.

If the molecule of interest is present in the sample, Raman scattered light will have experienced the various frequency shifts associated with the molecule's different vibrational states unique to its chemical structure, allowing the assumption that the molecule of interest is present in the sample. Optimally, a frequency shift is chosen which is particular to the molecule of interest and does not coincide with any of the Raman shifts of other molecules that may be found in the sample.

By optically filtering the scattered light and focusing upon a single frequency, it is possible to just use the amplitude of the measured signal and a predetermined threshold value to ascertain the presence or absence of a given molecule, without the need to obtain or characterize the total combined Raman spectrum of all the molecules present in the sample using software. If light falls on the detector 216 and the amplitude of the signal recorded is above the threshold value, then the molecule of interest is present in the sample; if no light falls on the detector 216 or the signal is below the threshold value, then the molecule is not present in the sample at a detectable level.

This threshold determination at a single frequency means that software processing is reduced to a simple yes/no determination. Furthermore, the CCD detector used in typical Raman spectrometers is replaced by a photodiode. The molecule of interest detected can be changed by changing the value of frequency that is optically filtered from the scattered light, requiring the substitution of one small component.

The same technique could apply to a device based on infrared absorption spectroscopy instead of Raman spectroscopy. Infrared absorption spectroscopy requires that infrared light covering a range of wavelengths be directed onto the sample. The wavelength range of interest is either scanned by using a monochromator, or the scanning is simulated by means of a technique called infrared Fourier Transform spectroscopy, which allows for all frequencies to be collected simultaneously in a large range. In this implementation, if there is only one predetermined molecule of interest in a sample, it would not be necessary to extract the full absorption spectrum of the sample. Rather, device 200 detects the absence of scattered light at a frequency corresponding to one of the dips in transmission associated with the molecule's different vibrational states. Thus, a device based on infrared absorption would be functionally similar to the one based on Raman scattering.

For example, using one technique, a filter or a combination of filters may be used to focus on the TCA, methanethiol, etc. response of the received signal. Various types of filtering techniques could be incorporated into the filtering element 214 of the detection system 208. For example, bandpass filters, notch filters, edge filters (long pass or short pass filters), etc. may be used to help isolate the response of the molecule of interest. Such filters may serve several purposes conducive to the isolation of the signal, e.g., narrowing the frequency of the incoming light, suppressing Rayleigh scattering, isolating a peak in the molecule of interest spectrum, etc. To suppress unwanted light signals, various types of processing techniques can be used. For example, calibration techniques may be used to first characterize signal sources other than molecule of interest (e.g., unwanted Raman scattering or fluorescence from the bottle, water molecules, etc.). Once characterized (e.g., within the frequency bands of interest), one or more processing techniques may be employed to substantially suppress, remove, etc. signal content associated with these unwanted sources. For example, estimation techniques, measurements, etc. may be used to determine the spectrum of the unwanted signal sources within the frequency bands of interest. Next, these determined spectral quantities represented by, e.g., amplitude, may be removed from the total signal response of the wine present in the bottle 100, leaving only the spectral response of the molecule of interest. In a sense, the data representing light signals (e.g., scattering or fluorescence) from unwanted sources can be removed enough to substantially isolate the signal gathered from the molecule of interest. Once isolated, the signal can be processed (e.g., by the software processing element 218, 224) to determine if the wine should be considered "corked" or appropriate for consumption.

Once this information is collected, processed, etc., additional operations and functionality may be employed. For example, one or more networking techniques (e.g., wireless networking) may be used to distribute the obtained data to other relevant persons (e.g., wine producers, distributors, etc.), facilities (e.g., storage sites, processing locations, etc.), etc. for dissemination and later use. The data may also be provided to facilities for storage, further analysis and presentation (e.g., on a web-based asset such as a website). The data may be used for a variety of applications, such as comparative studies, on-going wine storage transportation analysis, etc.

Characterization of Flavor Profiles—Big Data

Device 200 is capable of detecting wine molecules in a non-invasive manner, e.g., without opening the wine bottle 100. The device 200 can be used to determine the wine characteristics based on the particular blend and concentrations of wine molecules in the wine bottle 100.

The software processing element 218 that determines the characteristics of a wine in a bottle 100 can be linked to wine library 230. The wine library 230 is a database of information consisting of the actual molecular makeup of a bottle of wine, the molecular fingerprint of the complex liquid in a bottle 100. A library of molecular ID tags can be built to give the wine industry information on every bottle of wine produced and those already in existence.

In one implementation, a producer who finishes bottling the 2017 harvest and can determine the molecular makeup of each bottle produced by using device 200 and enter that information into a database or wine library 230. Such information can include basic or identifying data on each bottle, e.g., name, vineyard, vintage, location of bottling, serial number, as well as the molecular makeup of that bottle. The descriptive attributes become side details appended to the molecular ID tag that is acquired and uploaded when the bottle is physically scanned by device 200.

The wine library 230 can provide information about bottles in their current state. The wine library can also be used to detect and understand the development of a bottle of wine over time, without having to open the bottle and expose the wine to oxidation. A producer who is aging a wine before sale, or a purchaser who is aging a wine post-sale can re-scan a bottle using the device 200 year after year. By re-scanning the bottle, the user can monitor the changes over time. A producer can track how the wine is evolving in the bottle, and can better experiment with ideal storage conditions to produce a particularly desired molecular blend. If ideal storage conditions are determined, a scan of an ideal bottle at any one time provides the producer with a benchmark of how that particular wine should be performing. Similar bottles in different locations and with different storage and transport histories that are also scanned using device 200 can be compared to this benchmark and priced accurately. For example, a bottle that has changed hands multiple times in the ten years since leaving the winery could be scanned in 2027 to determine its molecular fingerprint. That molecular fingerprint could be compared with that of a bottle of the same vintage that was stored at the winery in a temperature-controlled cellar during the same decade. This ability would allow for the bottle in question to be correctly priced, with no guesswork involved, before opening the bottle. This would not only allow for accurate asset pricing but would also circumvent the reputation cost of an underperforming bottle for the particular winery.

Another application of multi-component fingerprint molecular wine analysis is the ability to identify counterfeit bottles of wine. Detected elevated levels of certain molecules like phenolic compounds, acids, ethanol, etc., could mean these substances were added and not derived from the grapes, which is not permitted in certain regions where fine wine is made. If a benchmark bottle molecular fingerprint is also available, the two scans could be compared.

Another application of multi-component fingerprint molecular wine analysis is the ability to generate descriptors of bottles of wine. By detecting various substances within the wine, the wine could be described, for example, using different taste metrics. In one example, a wine's structure could be described by assigning scores in percent or out of 10 based on the detected substances to various characteristics, such as acidity, alcohol, body, sweetness, tannin, etc.

Device 200 in communication with wine library 230 could give winemakers a powerful tool to track the long term outcome of winemaking decisions in a much more quantitative way. The wine library 230 allows for the molecular ID tag of a single bottle to be uploaded onto a database and its progress monitored as it ages. This ID tag could then be compared with the ID tag of, for instance, an equivalent bottle (same producer, vintage, etc.) about to be sold elsewhere after changing hands several times, and scanned on another device 200.

Creation of a wine library 230 also allows for a wine blockchain, or a distributed database that maintains a continuously growing list of records, or blocks, secured from tampering and revision. Blockchains are an open, distributed ledger that can record transactions between two parties efficiently and in a verifiable and permanent way. Each block could represent the molecular fingerprint of a single bottle of wine taken by device 200 at a particular time, and contains a timestamp and a link to a previous block, e.g., scan of that bottle by device 200 at an earlier time. By design, blockchains are inherently resistant to modification of the data since the data in a block cannot be altered retroactively once recorded. Such a feature helps the security, or provenance, or a particular bottle of wine. Such features can help counteract counterfeit. If combined with transaction records for each bottle (or for high value bottles), a wine blockchain could also prevent theft.

Machine Learning: Molecular Sommelier

Another source of transaction costs to a user purchasing wine is that wine is a complex blend of different molecules and a complicated mixture of tastes. The evaluation and description of wine uses subjective terms to describe the flavor profiles (for example "red fruit", "blackcurrants", "damp basement") that are not always clear to the casual drinker. Flavors that are very enjoyable to one taster, such as one who enjoys "damp basement", can be unpalatable to another. Device 200 can be used to advantageously characterize wine and describe that wine more precisely to a user, who can better evaluate if she would enjoy that particular bottle. Detailed molecular information for available wines (e.g., use of the wine library 230) can be used with machine learning techniques to develop highly precise taste profiles and recommendations for a purchaser based on the molecular mix of a particular bottle. Such a library and algorithm can function as a wine sommelier, detecting preferences and suggesting wines due to their molecular mix.

Figure 4:
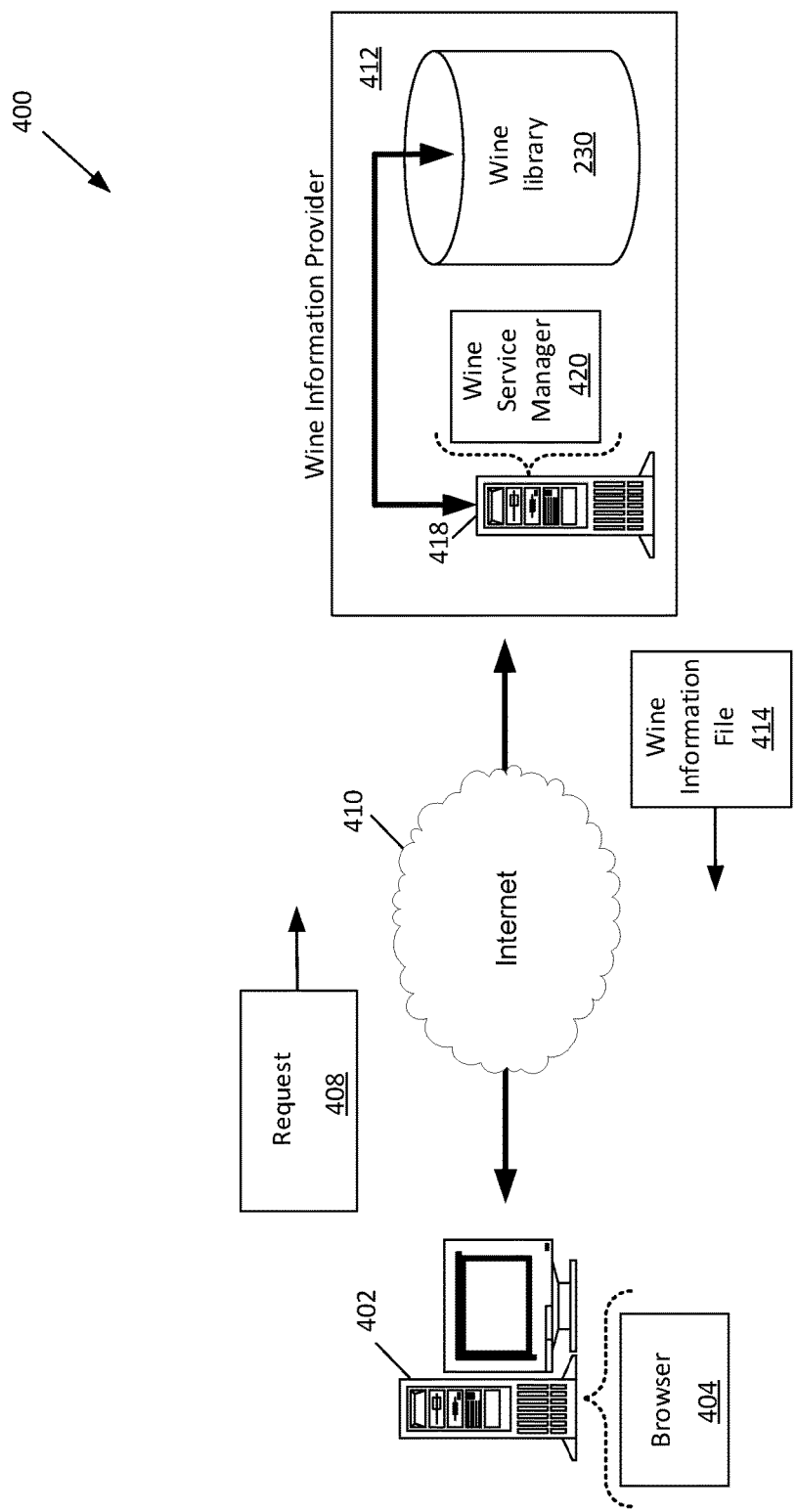
FIG. 4 is a block diagram of an Internet-based computer network that provides wine characteristic information.

Referring to FIG. 4, a computing environment 400 is presented that includes a computer system 402 that a user may interact with (using a keyboard, a pointing device, etc.) and which may execute one or more applications (e.g., a browser 404) for attaining wine information. New wines, which are produced yearly, become available for potential selection and use on the computer system 402 when they are evaluated using device 200 as described above and their molecular ID tag is entered into the wine library 230.

Similar to the browser 404, other types of executable objects may be used for attaining the appropriate wine information. For example, the computer system 402 may request appropriate wine information (e.g., wines determined to be similar to a selected focus wine) by sending a request 408 to attain the appropriate wine information.

In the computing environment 400, the request 408 is sent over one or more networks (e.g., the Internet 410) to a wine information provider 412 for processing (e.g., identifying and providing the requested wine information). Once the needed information is produced, one or more techniques may be implemented to provide it to the computer system 402. For example, one or more files, such as a wine information file 414, may be produced by the wine information provider 412 and sent to the computer system 402.

To provide the appropriate wine information to the computer system 402, the wine information provider 412 typically needs access to the wine library 230 which may be stored locally or remotely. For example, wine library 230 may be stored in memory devices (e.g., one or more hard drives, CD-ROMs, etc.). Being accessible by a server 418, the library may be used to attain the appropriate wine information (e.g., identify wines are similar to a focus wine). Illustrated as being stored in a single storage device 230, the wine information provider 412 may also use numerous storage techniques and devices to retain collections of wines and related wine information (e.g., for different wine styles, regions, etc.). Lists of wines and wines identified as being similar and one or more measures of similarities can also be stored. The wine information provider 412 may also access wine information at separate locations as needed. For example, along with identifying similar wines for the computer system 402, the server 418 may be used to collect needed information from one or more sources external to the wine information provider 412 (e.g., via the Internet 410).

Along with providing needed wine information, the wine information provider 412 may contribute other functions. For example, wine information may be prepared in advance by the wine information provider 412 for future use. For example, as new wines are developed, the wine information provider 412 may categorize the new wines and determine similarities with these wines and previously produced wines. Such preparation work could improve efficiency in providing wine information to the computer system 402 regarding a new wine. To provide this functionally, the server 418 executes a wine service manager 420, which, in general, manages the flow of received requests and the delivery of requested information. The wine service manager 420 also manages wines, data that represents similarities (or dissimilarities) among the wines, storage for later retrieval, etc. As such, similar wines may be quickly identified and provided to a requesting computing device (e.g., the computer system 402). In one arrangement, a database (or other technique for structuring and storing data) is stored at the wine information provider 412 (e.g., on the storage device 230) and includes records that represent the similarities (or dissimilarities) among wines. In some instances, the similarity information is identified in part from information provided by the request 408 (and other requests) sent to the wine information provider 412. Similarly, the wine information provider 412 may perform operations (e.g., tracking, monitoring, etc.) regarding other types of information. For example, records may be stored that reflect particular wines that have been requested from and provided to an individual person or user, or subscriber to the wine information provider 412.

Referring to FIG. 4, one or more techniques may be implemented to determine similarities between wines and provide identified wines to a computing device (e.g., the computer system 402). For such techniques, information may be used from one or more data sources. For example, data (e.g., survey data) may be collected that represents wine similarities as decided by individuals (e.g., potential wine purchasers). For one type of survey, individuals may be presented samples of three wines (e.g., wine A, wine B and wine C). After being allowed to review each, a query may be presented in which the user is asked to select which pair of wines are more similar (e.g., wines A and B are more similar or wines A and C are more similar). By collecting responses from a number of individuals for a variety of wine comparisons, noticeable trends may be detected among wines, wine families, etc. In some arrangements, randomly selected wines are used in the posed queries; however, other bases may be used (e.g., survey questions based on wine use for different platforms, wine sales data, etc.). In some examples, along with allowing the user to select which wine pair is more similar, the query may also provide a non-committal response (e.g., "Impossible to say") for filtering out situations in which a survey-taker is unable to clearly identify one wine pair as being more similar than another pair or when the wines in both pairs are radically different from each other. For another type of survey, data can be collected from interested third parties, for example, wine experts. The survey data, including, for example, descriptive words, can be used as training data.

In some implementations, such a survey technique can take place in person, e.g., during wine tastings that occur at a wine store or winery, and the user can develop her profile based on actual tastes of the moment. In some implementations, such surveys can take place remotely, such as online. In this instance a user can enter information based on past experiences related to particular bottles of wine. Alternatively, the user can enter a series of survey questions, e.g., "do you like blackcurrant notes" to generate this information.

Along with the collected similarity information (e.g., from survey takers), other techniques may be used in concert for determining wine similarities. One or more forms of artificial intelligence, such as machine learning, can be employed such that a computing process or device may learn to determine wine similarities from training data, without being explicitly programmed for the task. Using this training data, machine learning may employ techniques such as regression to estimate wine similarities. To produce such estimates, one or more quantities may be defined as a measure of wine similarity. For example, the level of difference between two wines may be defined as the sugar content between the wines. One or more conventions may be utilized to define such sugar content between wines; for example, a pair of wines that have a relatively close sugar content can be considered similar. Alternatively a wine pair that has a large sugar difference can be considered different. As such, upon being trained, a learning machine may be capable of outputting a numerical value that represents the sugar difference between two wines.

One or more techniques may be implemented to determine identification or components of wines, whether a particular bottle is made from a certain grape or varietal (or combination), from a particular producer, a particular vintage, from a particular geographical location, or all of the above.

To implement such an environment, one or more machine learning techniques may be employed. For example, supervised learning techniques may be implemented in which training is based on a desired output that is known for an input. Supervised learning can be considered an attempt to map inputs to outputs and then estimate outputs for previously unused inputs. Unsupervised learning techniques may also be used in which training is provided from known inputs but unknown outputs. Reinforcement learning techniques may also be employed in which the system can be considered as learning from consequences of actions taken (e.g., inputs values are known and feedback provides a performance measure). In some arrangements, the implemented technique may employ two or more of these methodologies. For example, the learning applied can be considered as not exactly supervised learning since the distance value between two wines can be considered unknown prior to executing computations. While the distance value is unknown, the implemented techniques can check the computed wine distances in concert with the collected survey data (e.g., in which a viewer identified if wine A is closer to wine B or to wine C). By using both information sources regarding wine similarity, reinforcement learning technique can be considered as being implemented.

In some arrangements, neural network techniques may be implemented using the survey as well as wine data (e.g., vectors of numerical values that represent features of the wines) to invoke training algorithms for automatically learning the wines and related information, such as wine similarity (e.g., sugar values, tannin content, etc.). Such neural networks typically employ a number of layers. Once the layers and number of units for each layer is defined, weights and thresholds of the neural network are typically set to minimize the prediction error through training of the network. Such techniques for minimizing error can be considered as fitting a model (represented by the network) to the training data. By using the survey data and the wine data (e.g., wine feature vectors), a function may be defined that quantifies error (e.g., a squared error function used in regression techniques). By minimizing error, a neural network may be developed that is capable of estimating wine similarity. Other factors may also be accounted for during neutral network development. For example, a model may too closely attempt to fit data (e.g., fitting a curve to the extent that the modeling of an overall function is degraded). Such overfitting of a neural network may occur during the model training and one or more techniques may be implements to reduce its effects.

Illustrated in FIG. 4, the wine service manager 420 is executed by the server 418 present at the wine information provider 412. In this arrangement, the wine service manager 420 includes a wine survey collector that is capable of retrieving data that represents wine similarity selections as provided from survey-takers. In this arrangement, such data may be previously stored (e.g., in a wine survey database 302) and retrieved from the wine library 230. Data representing such survey information may also be retrieved from one or more sources external to the wine information provider 412; for example such information may be attained from one or more storage devices of a survey manager (e.g., an entity separate from the wine information provider 412). Along with survey information, the wine library 230 (or other storage devices at the wine information provider 412) may contain a wine database 304 that includes information about previously produced wines and newly introduced wines. From the information stored in the wine library 230, data may be retrieved for learning machine training and use, e.g., to determine wine similarity (e.g., determine the distance between wine pairs, etc.). For example, the wine library 230 may include data that represents various types of wine families (e.g., white, red, etc.) that can include wine varietals (e.g., Shiraz, Riesling, etc.). Data for each wine may represent a set of molecules and the ranges present for each molecule associated with the wine.

A variety of wine features may be used for training and machine learning. For example, tens of features (e.g., 30, 40 features) may be calculated for each wine. For example, features may include the most common molecules found in wines. Generally when a wine ages, the tannins present polymerize leading to changes in the flavor profile changes as certain compounds arise through very slow chemical reactions or become more prominent and the acidity reduces. The set of molecules can include acetaldehyde, sotolon (a lactone that gives a walnut aroma), furaldehyde (gives almond aroma), cyclotene (part of coffee/chocolate aroma), 2-nonenal (hay aroma), phenylacetaldehyde (honey aroma), etc. Other aroma compounds associated with lees or malolactic fermentation or oak, could be used to predict, for example, if the Chardonnay contained in a bottle is a steely unoaked Chablis that has undergone bâtonnage (lees stirring) or a blowsy oaked Pouilly Fuissé.

In some implementations, spectroscopic data obtained using any of the techniques described herein and survey based data can be used simultaneously.

Other features of interest can include a score or rating for that wine, for example the Wine Spectator score, as assessment of when is the wine ready to drink, oxidation or training sets, or any of the suite of molecules that indicate wine development.

Determined wine features may be processed prior to being used for machine training (or for use by a trained machine to determine wine similarity). For example, a vector that represents a collection of wine features may be normalized so that training data used can be considered as being placed on an equal basis (and one or more particular wine features are not over emphasized). Such normalizing operations may take many forms. For example, the estimated value (e.g., average) and standard deviation (or variance) may be calculated for each feature vector (e.g., by calculating an average and standard deviation of the features included in the vector). Once these quantities are calculated (e.g., the average and standard deviation) each of feature in the vector may be normalized, for example, by using an equation:

Once trained, the wine service manager 420 may be used to determine the similarity between pairs of wines (not used to train the machine). The wine service manager 420 can calculate and compare the concentration of a molecule between the wines as a measure of similarity.

Along with calculating wine distance values and other quantities, the wine service manager 420 may provide other types of functionality. The wine service manager 420 may also initiate the storage of data that represents the determined wine preferences. Storing such data generally allows the information to be quickly retrieved rather than being recalculated. For example, for each wine residing at the wine information provider 412, a list of similar wines (e.g., the closest ten wines) may be produced and stored for quick retrieval. By caching such information, lists of similar wines may be quickly attained. Additionally, as newly introduced wines appear (e.g., are produced and provided to the wine information provider 412 after evaluation by device 200) operations may be executed to keep the wine similarity database updated. Techniques such as batch processing may be implemented for calculating the similarity levels (e.g., presence of particular molecules) between the newly introduced and previously existing wines. In some situations multiple new wines may be introduced together and techniques may be employed to efficiently determine similarity levels with preexisting wines. For example, preexisting wines may be retrieved one-by-one and operations to determine a similarity level with each of the new wines. By implementing batch processing or other similar techniques, updating of the databases stored at that wine information provider 412 may be executed during less busy time periods (e.g., overnight).

Collection and Detection Methods

As discussed above, there are several possible methods of illuminating and extracting scattered and transmitted light from a sealed glass bottle. Below describes four methods of coupling the light in and out of the bottle, and two methods of collecting and filtering the acquired signal. Implementation details of these methods may differ for absorption spectroscopy and for Raman spectroscopy. Each of these techniques can be implemented in a housing structure that provides a convenient interface between the components of the detection device and the bottle.

Figure 5:
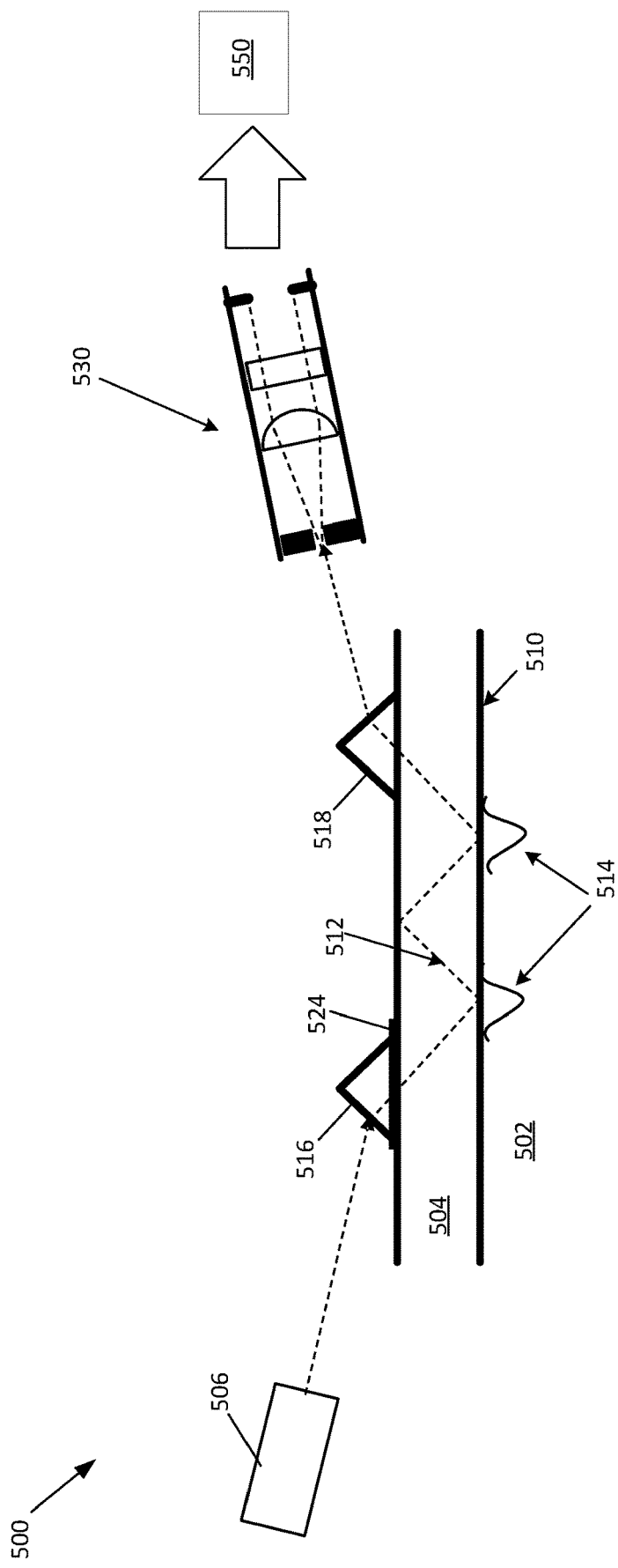
FIGS. 5-7 illustrate systems for coupling a light to a bottle for wine signal detection.

FIG. 5 shows a coupling method 500 used to obtain an absorption spectrum from wine 502 inside a bottle wall 504 (typically a glass bottle). Broadband light from a broadband light source 506 (which can be visible, supercontinuum, infrared, free space, or fiber-coupled) is aimed at the glass/wine interface 510. The light is directed to be incident on the bottle wall 504 at the "critical angle" causing total internal reflection, where the light beam 512 from the light source 506 propagates within the bottle wall 504 without ever entering the wine 502. Every time the light beam 512 bounces off the inner wall of the bottle at the glass/wine interface 510, there is an evanescent field or wave 514 which "leaks" into the wine 502. Although the light 512 does not enter the wine 502 directly, there is nevertheless an interaction with the wine 502 which leads to absorption.

Two beam-redirecting object, namely prisms 516, 518 are used to couple the light beam 512 emitted from the light source 506 to the bottle wall 504 and then through collection optics 530 to a spectrometer 550. The light beam 512 is incident on the first prism 516, where it is refracted into the bottle wall 504. The light beam 512 is extracted from the bottle wall 504 using the second prism 518, which redirects the beam from where it has been bouncing within the bottle wall 504 due to total internal refraction outwards towards the spectrometer 550. An index-matching material 524 for connecting the prisms 516, 518 (e.g., a material whose index of refraction corresponds to the index of refraction of the glass of the bottle wall 504) may be used to obtain a seamless optical interface. In some instances, the refractive index matching element may be a gel or an optically transparent polymer.

Figure 6:
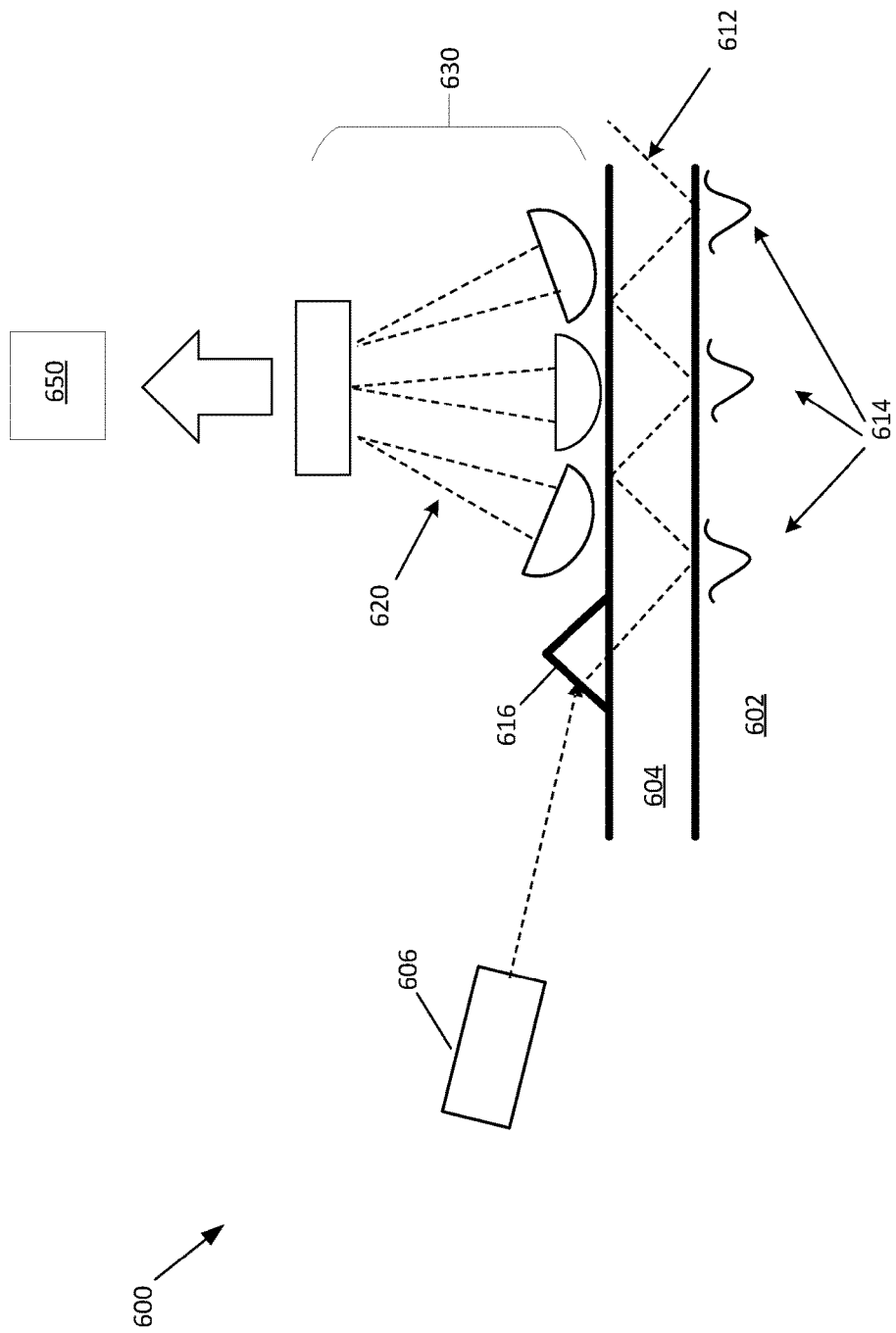

FIG. 6 shows a second coupling method 600 used to obtain a Raman spectrum from wine 602 inside a bottle wall 604. Similar to as in FIG. 5, light from a light source 606 is incident on the bottle wall 604 at the critical angle causing total internal reflection such that the light beam 612 propagates within the bottle wall 604 without ever entering the wine 602 or re-entering the ambient air. Here, the light is typically monochromatic light (e.g., the light source 606 is a laser). The light beam 612 is incident on a single prism 616, where it is refracted into the bottle wall 604. Every time the light beam 612 bounces off the inner wall of the bottle at the glass/wine interface, there is an evanescent field or wave 614 which propagates into the wine 602. Although the light beam 612 does not enter the wine 602 directly, there is nevertheless an interaction with the wine, which leads to Raman scattering. Raman scattered light 620 from one or more of these bounces is collected from outside the glass wall 604 (e.g., via appropriate collection optics 630) and sent to a spectrometer 650. In this case, the principal light beam 612 is of no interest and simply propagates within the bottle wall 604 without ever being directed outwards. An index-matching material for the prism 616 may be used to obtain a seamless optical interface.

Figure 7:
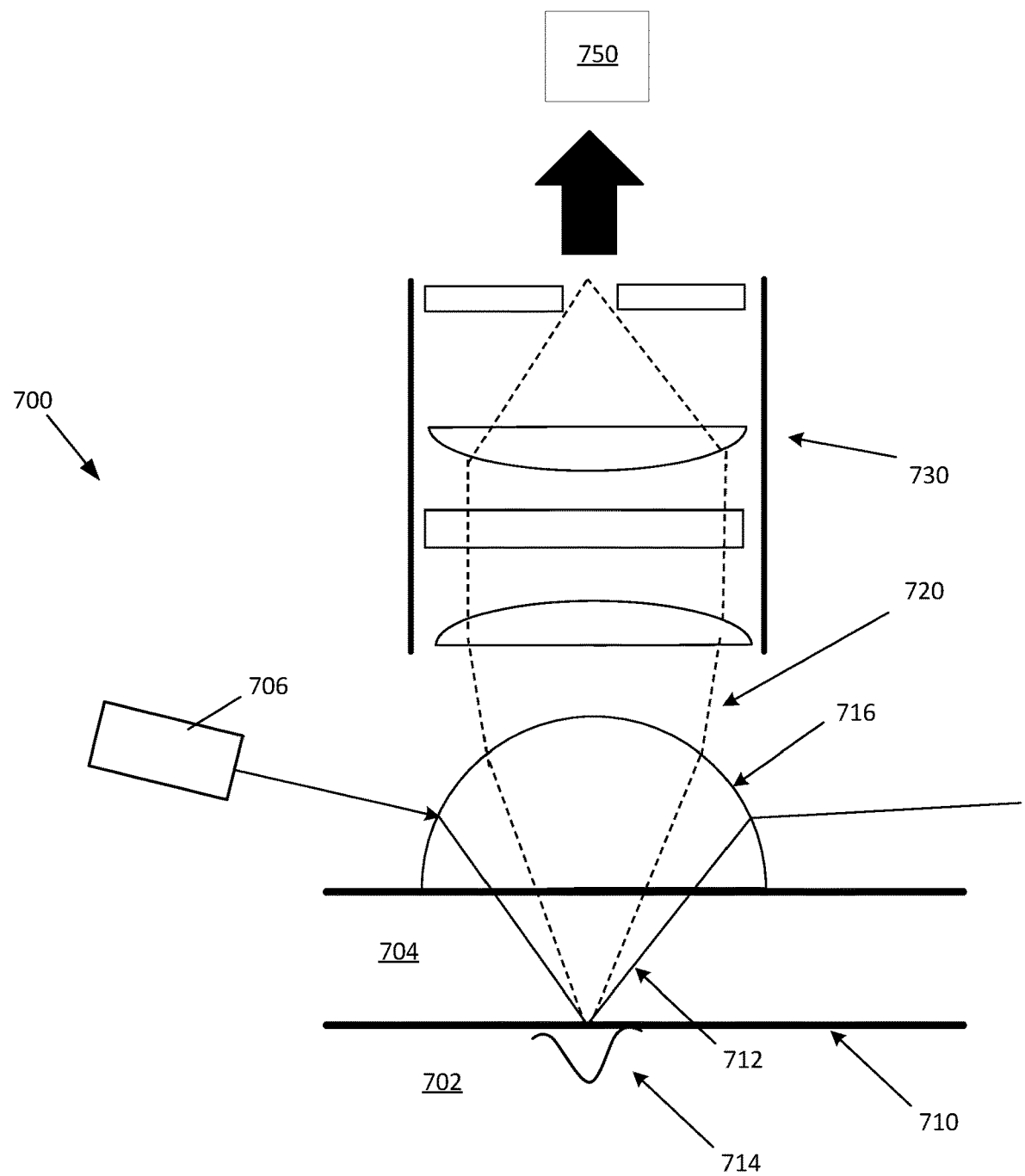

FIG. 7 shows another coupling method 700 used to obtain a Raman spectrum from wine 702 inside a bottle wall 704. Similar to as in FIG. 6, a light beam 712 from a light source 706 (typically monochromatic light from a laser) is incident on the bottle wall 704 to cause total internal reflection. The light beam 712 is incident on a ball lens 716 (or cylindrical lens) that reflects it into the bottle wall 704. The light beam 712 bounces off the inner wall of the bottle at the glass/wine interface 710 once, causing a single evanescent field 714 that propagates into the wine 702 and leads to Raman scattering. After reflecting off the glass/wine interface 710, the light beam 712 again is incident on the ball lens 716 and directed away from the bottle and the spectrometer 750 so as not to confuse the signal detected. Raman scattered light 720 from the single bounce is collected via the same ball lens 716 along the axis perpendicular to the plane of interaction. This arrangement has the advantage of narrowing the scattering angle of the light and facilitating collection by further collection optics 730 before it impinges on the spectrometer 750. An index-matching material for the ball lens 716 may be used to obtain a seamless optical interface.

Figure 8:
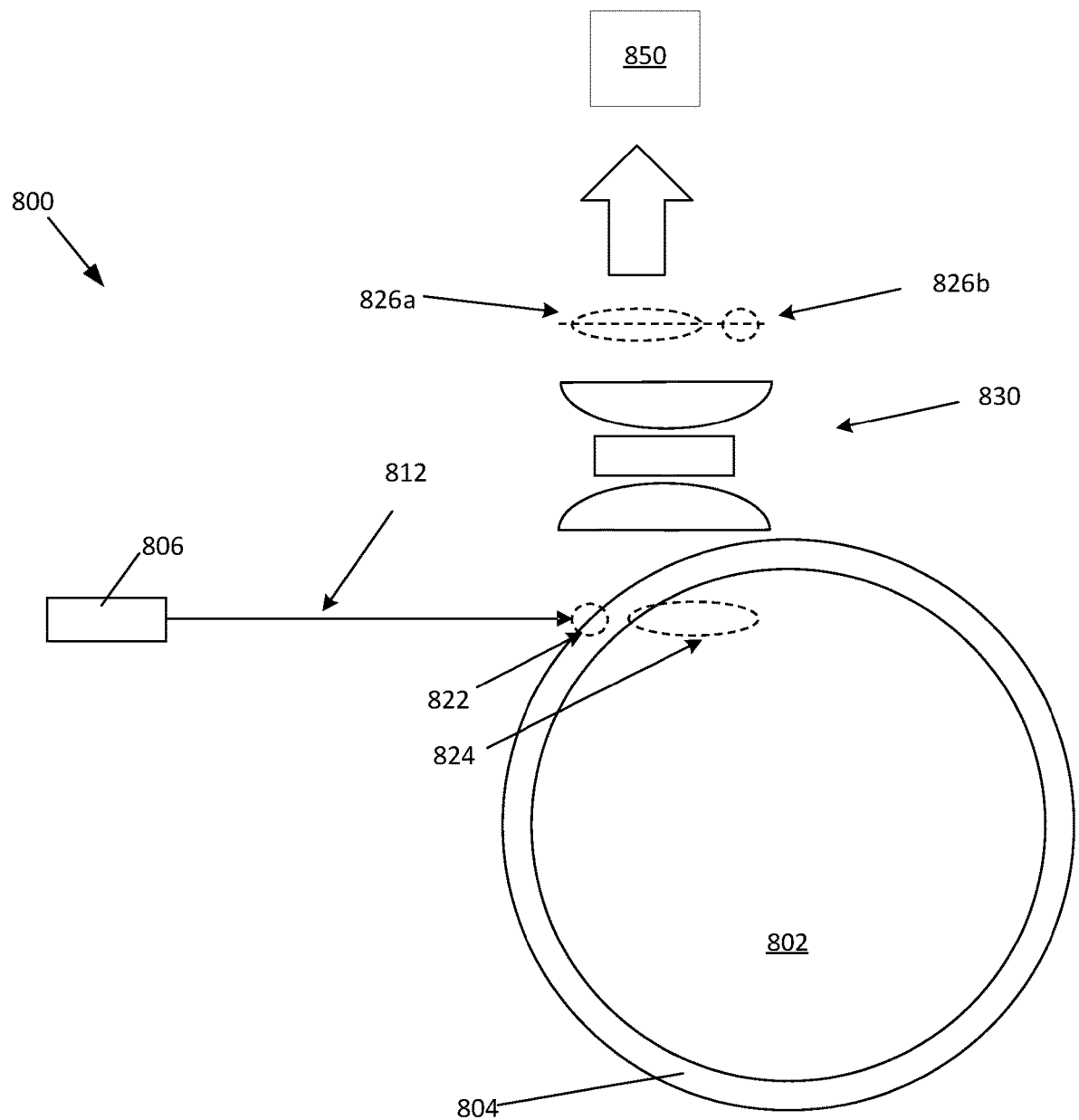
FIG. 8 illustrate a system for coupling a light to a bottle for wine signal detection and a system for detecting Raman signals.

FIG. 8 shows a setup 800 with the bottle in cross section. The setup 800 can be used to obtain a Raman spectrum from wine 802 inside a bottle wall 804, similar to the methods discussed above. Light beam 812 from a light source 806 (typically monochromatic light from a laser) is incident on the bottle wall 804. However, there is no optical element to interface the light with the bottle wall 804. Unlike in the methods above, the light beam 812 does penetrate the wine 802. However, the angle of incidence between the light beam 812 and the bottle wall 804 is very shallow, minimizing the Raman interaction inside the wine 802. The angle of incidence is chosen such that a bottle interaction volume 822 that produces Raman scattering from the bottle wall 804 and a wine interaction volume 824 that produces Raman scattering from the wine are as close as possible to the glass wall.

FIG. 8 also shows a first detection method to capture the Raman signal in setup 800. The scattered light travels outside the bottle wall 804 to the collection optics 830. The collection optics 830 are configured to generate a space-resolved image 826a of the wine interaction volume 824 and a separate space-resolved image 826b of the wall interaction volume 822. The image 826a of the wine interaction volume 824 alone can be directed into the spectrometer 850, allowing it to be analyzed separately and more efficiently than when combined with signals generated by the bottle wall 804.

Figure 9:
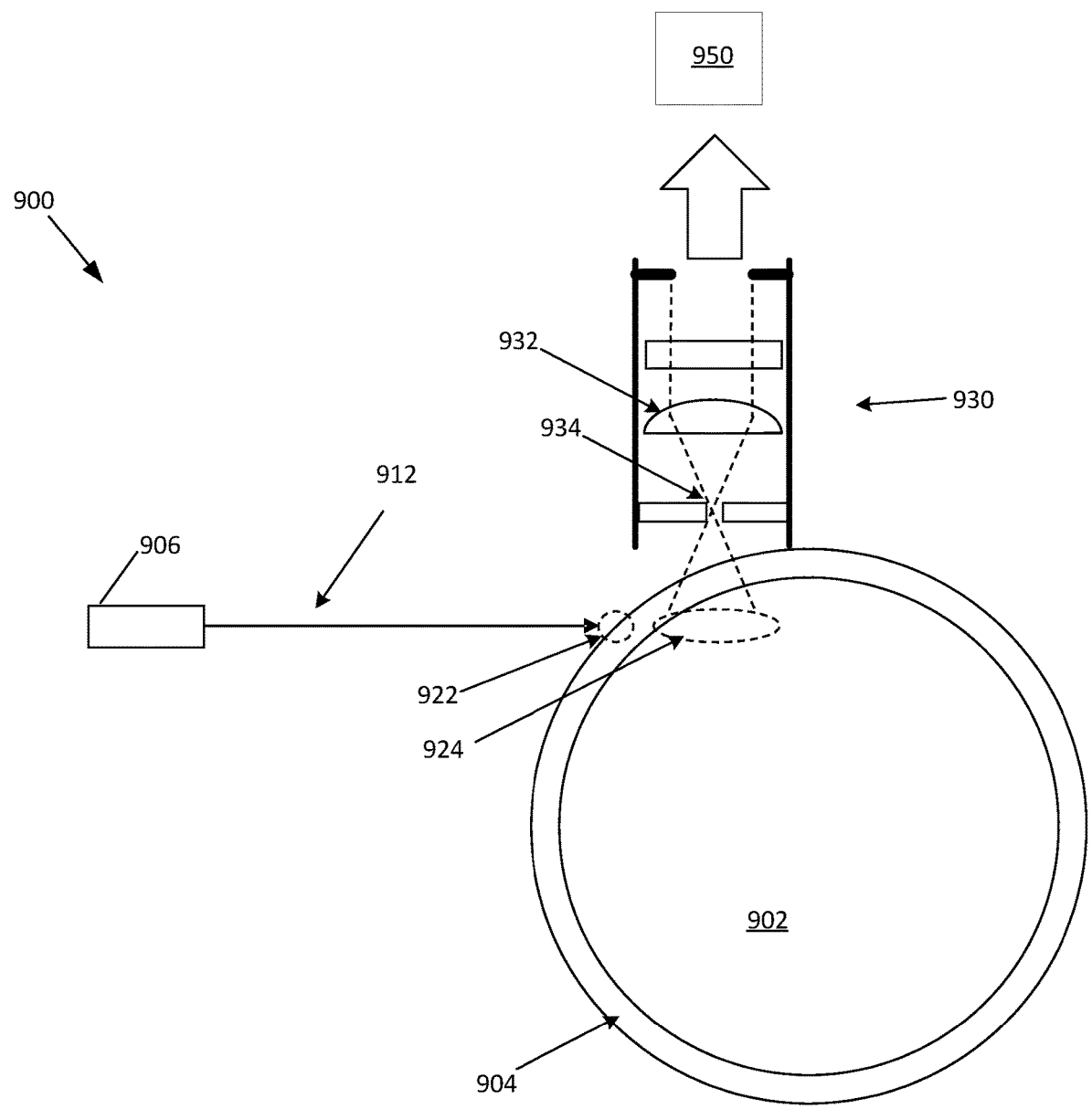
FIG. 9 illustrate systems for detecting Raman signals.

FIG. 9 shows a second detection setup 900 used to obtain a Raman spectrum that can also be used in combination with the coupling method described with respect to FIG. 8, with the many of the same components (namely wine 902, bottle wall 904, light source 906, light beam 912, interaction volumes 922, 924 and spectrometer 950). The detection setup 900 can be used with any of the coupling methods described in reference to FIGS. 6-8.

Generally, the wall interaction volume 922 and the wine interaction volume 924 are non-overlapping regions. In detection setup 900, the collection optics 930 can include suitable optics (e.g., a slit 934) to image the bottle interaction volume 922 and wine interaction volume 924 separately. The collection optics 930 can be adjusted so that the pinhole or slit 934 serves as a limiting aperture which allows for the light from a single interaction volume 922, 924 to be detected. The Raman signal from the bottle wall 904 and the Raman signal from the wine 902 can thereby be spectrally separated and analyzed separately and more efficiently.

Figure 10A:
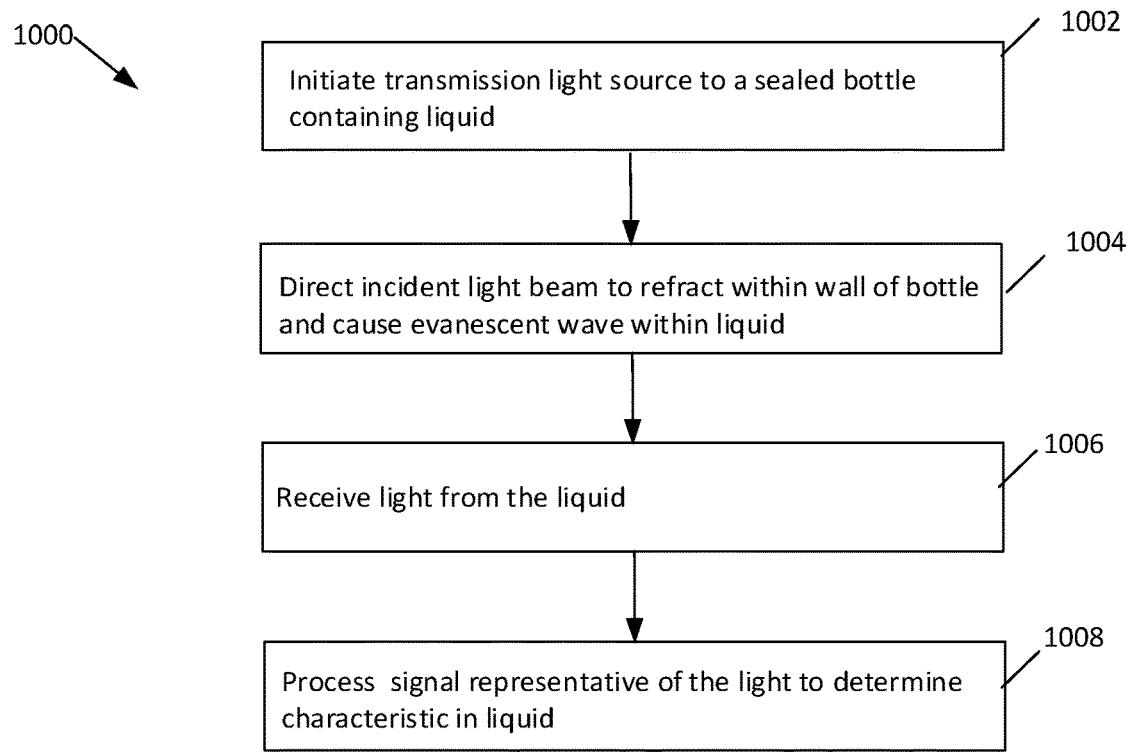
FIGS. 10A-B are example flow charts of operations for detecting wine characteristics.

Referring to FIG. 10A, a flowchart 1000 illustrates the operations of the liquid fault detection system (e.g., the light source 202, the optical sampling/filtering element 210 and the detection system 208 shown in FIG. 2). Operations of the fault detection system are typically executed by a single device (e.g., the device 200). However, operations may also be executed by multiple devices. Operations of the liquid fault detection system may include step 1002, initiating transmission of an incident light beam from a light source to the sealed bottle. For example, a wine bottle (e.g. the wine bottle 100) may be illuminated as initiated by a light source incorporated into a device (e.g., a laser, LED, etc. provided by the light source 506 of the device 200). Operations also include step 1004, directing the incident light beam to totally internally refract within a wall of the sealed bottle and thereby cause an evanescent wave within the liquid to generate scattered or absorbed light receiving. For example, the redirection can be caused by a prism 516. Operations also include step 1006, receiving the scattered or absorbed light from the liquid contained in the sealed bottle, for example at spectrometer 550, and processing one or more signals representative of the scattered or absorbed light, the signals indicative of one or more molecules indicative of a characteristic being present in the liquid contained in the sealed bottle, step 1008.

Figure 10B:
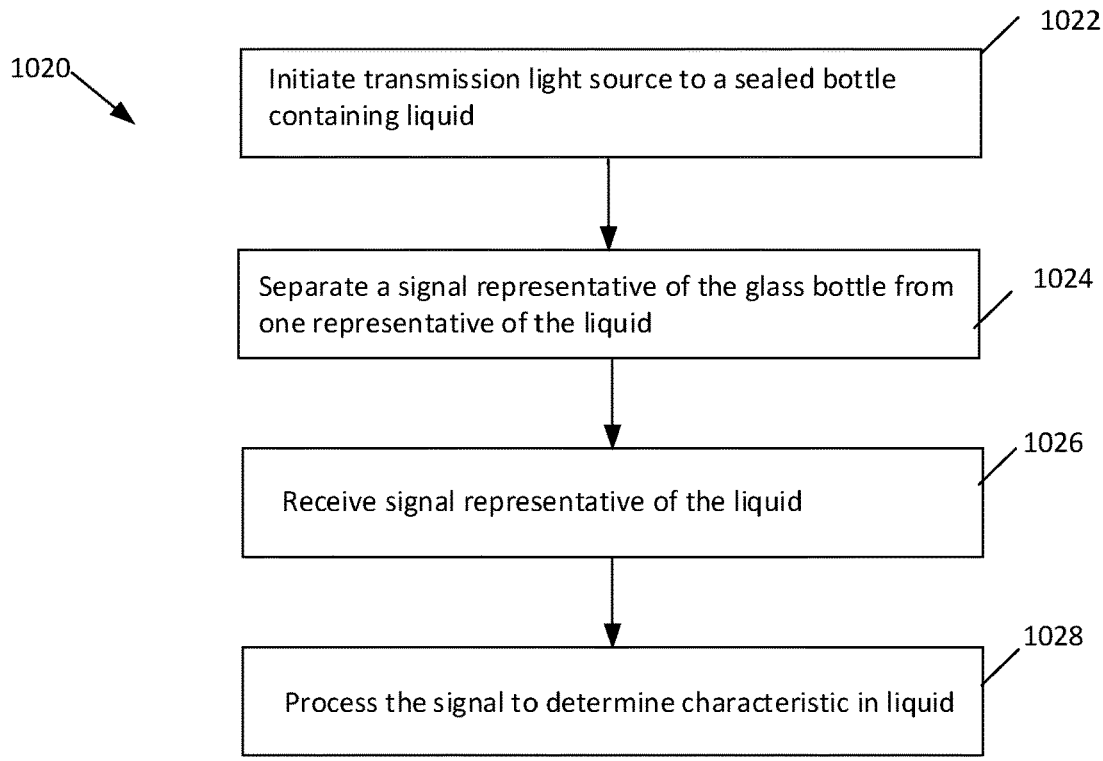

Referring to FIG. 10B, a flowchart 1000 illustrates further operations of the liquid fault detection system (e.g., the light source 202, the optical sampling/filtering element 210 and the detection system 208 shown in FIG. 2). Operations of the fault detection system are typically executed by a single device (e.g., the device 200). However, operations may also be executed by multiple devices. Operations of the liquid fault detection system may include step 1022, initiating transmission of an incident light beam from a light source to the sealed bottle and generate scattered or absorbed light. For example, a wine bottle (e.g. the wine bottle 100) may be illuminated as initiated by a light source incorporated into a device (e.g., a laser or light source 906). Operations also include step 1024, separating a signal representative of light scattered or absorbed by the glass bottle and a signal representative of light scattered or absorbed by the liquid, for example using optics 930. Operations also include step 1026, receiving the signal representative of light scattered or absorbed by the liquid the scattered or absorbed light from the liquid contained in the sealed bottle, for example at spectrometer 950. Step 1028 involves processing the signal representative of light scattered or absorbed by the liquid, the signal indicative of one or more molecules indicative of a characteristic being present in the liquid contained in the sealed bottle.

Figure 11:
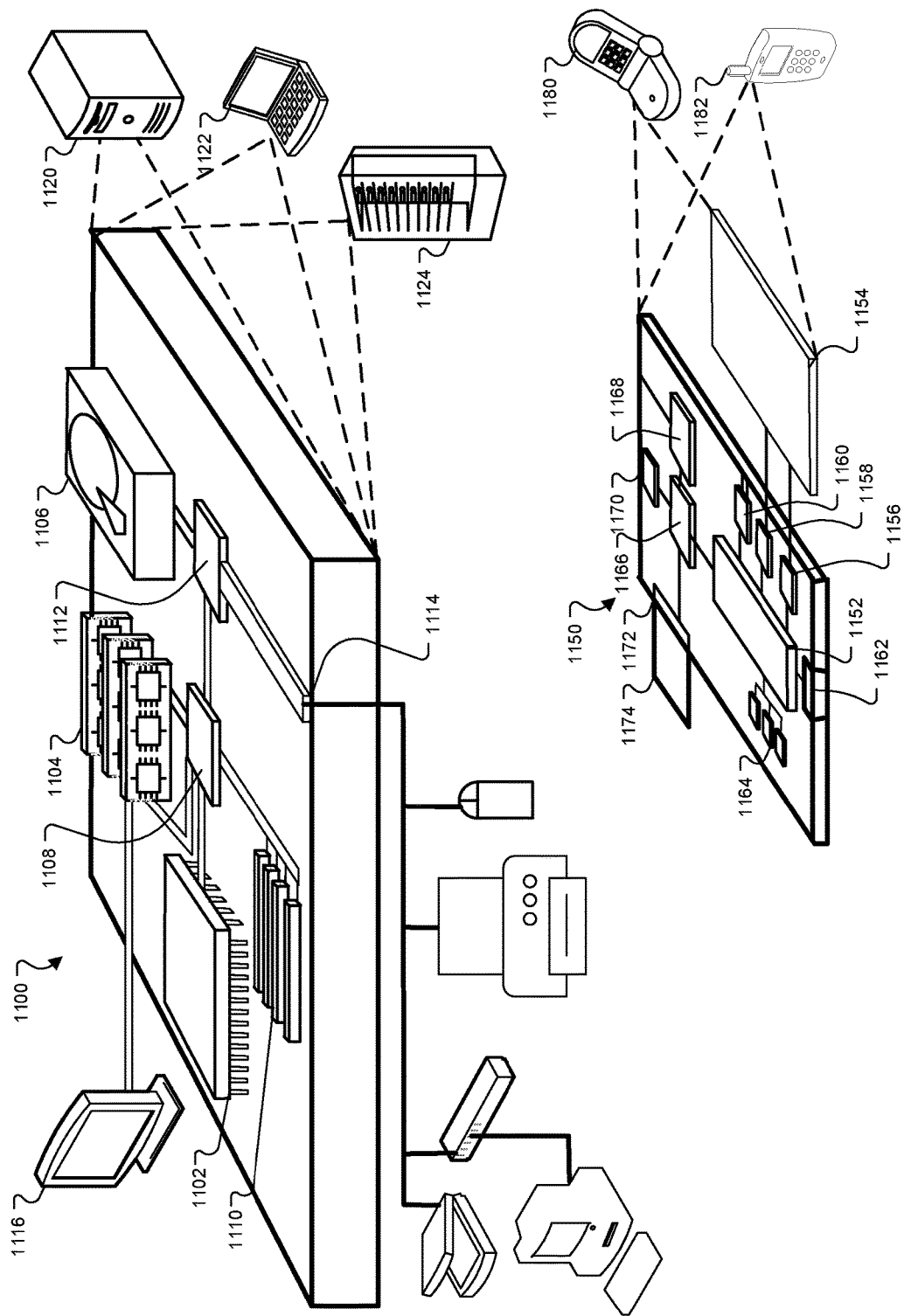
FIG. 11 illustrates an example of a computing device and a mobile computing device that can be used to implement the techniques described here.

FIG. 11 shows an example computer device 1100 and example mobile computer device 1150, which can be used to implement the techniques described herein. For example, a portion or all of the operations of wine analysis may be executed by the computer device 1100 and/or the mobile computer device 1150. Computing device 1100 is intended to represent various forms of digital computers, including, e.g., laptops, desktops, workstations, personal digital assistants, servers, blade servers, mainframes, and other appropriate computers. Computing device 1150 is intended to represent various forms of mobile devices, including, e.g., personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 1100 includes processor 1102, memory 1104, storage device 1106, high-speed interface 1108 connecting to memory 1104 and high-speed expansion ports 1110, and low speed interface 1112 connecting to low speed bus 1114 and storage device 1106. Each of components 1102, 1104, 1106, 1108, 1110, and 1112, are interconnected using various busses, and can be mounted on a common motherboard or in other manners as appropriate. Processor 1102 can process instructions for execution within computing device 1100, including instructions stored in memory 1104 or on storage device 1106, to display graphical data for a GUI on an external input/output device, including, e.g., display 1116 coupled to high speed interface 1108. In other implementations, multiple processors and/or multiple buses can be used, as appropriate, along with multiple memories and types of memory. Also, multiple computing devices 1100 can be connected, with each device providing portions of the necessary operations (e.g., as a server bank, a group of blade servers, or a multi-processor system).

Memory 1104 stores data within computing device 1100. In one implementation, memory 1104 is a volatile memory unit or units. In another implementation, memory 1104 is a non-volatile memory unit or units. Memory 1104 also can be another form of computer-readable medium, including, e.g., a magnetic or optical disk.

Storage device 1106 is capable of providing mass storage for computing device 1100. In one implementation, storage device 1106 can be or contain a computer-readable medium, including, e.g., a floppy disk device, a hard disk device, an optical disk device, a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 1104, storage device 1106, memory on processor 1102, and the like.

High-speed controller 1108 manages bandwidth-intensive operations for computing device 1100, while low speed controller 1112 manages lower bandwidth-intensive operations. Such allocation of functions is an example only. In one implementation, high-speed controller 1108 is coupled to memory 1104, display 1116 (e.g., through a graphics processor or accelerator), and to high-speed expansion ports 1110, which can accept various expansion cards (not shown). In the implementation, the low-speed controller 1112 is coupled to storage device 1106 and low-speed expansion port 1114. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router (e.g., through a network adapter).

Computing device 1100 can be implemented in a number of different forms, as shown in the figure. For example, it can be implemented as standard server 1120, or multiple times in a group of such servers. It also can be implemented as part of rack server system 1124. In addition or as an alternative, it can be implemented in a personal computer (e.g., laptop computer 1122). In some examples, components from computing device 1100 can be combined with other components in a mobile device (not shown) (e.g., device 1150). Each of such devices can contain one or more of computing device 1100, 1150, and an entire system can be made up of multiple computing devices 1100, 1150 communicating with each other.

Computing device 1150 includes processor 1152, memory 1164, and an input/output device including, e.g., display 1154, communication interface 1166, and transceiver 1168, among other components. Device 1150 also can be provided with a storage device, including, e.g., a microdrive or other device, to provide additional storage. Components 1150, 1152, 1164, 1154, 1166, and 1168, may each be interconnected using various buses, and several of the components can be mounted on a common motherboard or in other manners as appropriate.

Processor 1152 can execute instructions within computing device 1150, including instructions stored in memory 1164. The processor can be implemented as a chipset of chips that include separate and multiple analog and digital processors. The processor can provide, for example, for the coordination of the other components of device 1150, including, e.g., control of user interfaces, applications run by device 1150, and wireless communication by device 1150.

Processor 1152 can communicate with a user through control interface 1158 and display interface 1156 coupled to display 1154. Display 1154 can be, for example, a TFT LCD (Thin-Film-Transistor Liquid Crystal Display) or an OLED (Organic Light Emitting Diode) display, or other appropriate display technology. Display interface 1156 can comprise appropriate circuitry for driving display 1154 to present graphical and other data to a user. Control interface 1158 can receive commands from a user and convert them for submission to processor 1152. In addition, external interface 1162 can communicate with processor 1142, so as to enable near area communication of device 1150 with other devices. External interface 1162 can provide, for example, for wired communication in some implementations, or for wireless communication in other implementations. Multiple interfaces also can be used.

Memory 1164 stores data within computing device 1150. Memory 1164 can be implemented as one or more of a computer-readable medium or media, a volatile memory unit or units, or a non-volatile memory unit or units. Expansion memory 1174 also can be provided and connected to device 850 through expansion interface 1172, which can include, for example, a SIMM (Single In Line Memory Module) card interface. Such expansion memory 1174 can provide extra storage space for device 1150, and/or may store applications or other data for device 1150. Specifically, expansion memory 1174 can also include instructions to carry out or supplement the processes described above and can include secure data. Thus, for example, expansion memory 1174 can be provided as a security module for device 1150 and can be programmed with instructions that permit secure use of device 1150. In addition, secure applications can be provided through the SIMM cards, along with additional data, including, e.g., placing identifying data on the SIMM card in a non-hackable manner.

The memory can include, for example, flash memory and/or NVRAM memory, as discussed below. In one implementation, a computer program product is tangibly embodied in a data carrier. The computer program product contains instructions that, when executed, perform one or more methods, including, e.g., those described above. The data carrier is a computer- or machine-readable medium, including, e.g., memory 1164, expansion memory 1174, and/or memory on processor 1152, which can be received, for example, over transceiver 1168 or external interface 1162.

Device 1150 can communicate wirelessly through communication interface 1166, which can include digital signal processing circuitry where necessary. Communication interface 1166 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 1168. In addition, short-range communication can occur, including, e.g., using a Bluetooth®, Wi-Fi, or other such transceiver (not shown). In addition, GPS (Global Positioning System) receiver module 1170 can provide additional navigation- and location-related wireless data to device 1150, which can be used as appropriate by applications running on device 1150.

Device 1150 also can communicate audibly using audio codec 1160, which can receive spoken data from a user and convert it to usable digital data. Audio codec 1160 can likewise generate audible sound for a user, including, e.g., through a speaker, e.g., in a handset of device 1150. Such sound can include sound from voice telephone calls, recorded sound (e.g., voice messages, music files, and the like) and also sound generated by applications operating on device 1150.

Computing device 1150 can be implemented in a number of different forms, as shown in the figure. For example, it can be implemented as cellular telephone 1180. It also can be implemented as part of smartphone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system. This includes at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for presenting data to the user, and a keyboard and a pointing device (e.g., a mouse or a trackball) by which the user can provide input to the computer. Other kinds of devices can be used to provide for interaction with a user as well. For example, feedback provided to the user can be a form of sensory feedback (e.g., visual feedback, auditory feedback, or tactile feedback). Input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such backend, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

A number of embodiments have been described. Nevertheless, it will be understood that various modifications can be made without departing from the spirit and scope of the processes and techniques described herein. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method of illuminating and extracting scattered and transmitted light from a liquid within a sealed bottle, the method comprising:
   initiating transmission of an incident light beam from one or more light sources to the sealed bottle;
   directing the incident light beam into the liquid within the sealed bottle at a first position to cause the liquid to generate scattered light and a wall of the sealed bottle to generate scattered light;
   receiving, from a second position that is different than the first position, the scattered light from the liquid and the scattered light from the wall;
   separating the scattered light from the liquid and the scattered light from the wall into one or more first signals representative of a first space-resolved image of the liquid and one or more second signals representative of a second space-resolved image of the wall, the first and second images comprising spatially separated images; and
   processing the one or more first signals to detect one or more molecules indicative of a characteristic being present in the liquid contained in the sealed bottle.

2. The method of claim 1, wherein directing the light beam comprises directing the light beam at a shallow angle of incidence with respect to the wall.

3. The method of claim 1, comprising spectrally separating the one or more first signals from the one or more second signals.

4. The method of claim 2, wherein the angle of incidence causes scattering from a portion of the liquid close to the wall.

5. The method of claim 1, wherein receiving the scattered light from the liquid and the scattered light from the wall comprises directing the scattered light from the liquid and the scattered light from the wall through optics toward a spectrometer.

6. A system for illuminating and extracting scattered and transmitted light from a liquid within a sealed bottle, the system comprising:
   a light source configured to allow initiation of transmission of an incident light beam to the sealed bottle;
   one or more optical elements configured to:
   direct the incident light beam into the liquid within the sealed bottle at a first position to cause the liquid to generate scattered light and a wall of the sealed bottle to generate scattered light,
   receive, from a second position that is different than the first position, the scattered light from the liquid and the scattered light from the wall, and
   separate the scattered light from the liquid and the scattered light from the wall into one or more first signals representative of a first space-resolved image of the liquid and one or more second signals representative of a second space-resolved image of the wall, the first and second images comprising spatially separated images; and
   a processor configured to process the one or more first signals to detect one or more molecules indicative of a characteristic being present in the liquid contained in the sealed bottle.

7. The system of claim 6, wherein directing the light beam comprises directing the light beam at a shallow angle of incidence with respect to the wall.

8. The system of claim 6, comprising spectrally separating the one or more first signals from the one or more second signals.

9. The system of claim 7, wherein the angle of incidence causes scattering from a portion of the liquid close to the wall.

10. The system of claim 6, wherein receiving the scattered light from the liquid and the scattered light from the wall comprises directing the scattered light from the liquid and the scattered light from the wall through the one or more optical elements toward a spectrometer.

11. The method of claim 1, wherein a lens is configured to separate the scattered light from the liquid and the scattered light from the wall.

12. The method of claim 1, wherein an aperture is configured to separate the scattered light from the liquid and the scattered light from the wall.

13. The system of claim 6, wherein the one or more optical elements include a lens configured to separate the scattered light from the liquid and the scattered light from the wall.

14. The system of claim 6, wherein the one or more optical elements include an aperture configured to separate the scattered light from the liquid and the scattered light from the wall.

* * * * *